(12) United States Patent
Mandecki et al.

(10) Patent No.: US 10,174,358 B2
(45) Date of Patent: Jan. 8, 2019

(54) ASSAY FOR IDENTIFICATION OF THERAPEUTICS TARGETING TERNARY COMPLEX FORMATION IN PROTEIN SYNTHESIS

(71) Applicant: Rutgers, The State University of New Jersey, New Brunswick, NJ (US)

(72) Inventors: Wlodek Mandecki, Princeton Jct., NJ (US); Emanuel Goldman, Montclair, NJ (US); Maxim Chudaev, Providence, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 359 days.

(21) Appl. No.: 14/529,618

(22) Filed: Oct. 31, 2014

(65) Prior Publication Data
US 2015/0118678 A1    Apr. 30, 2015

Related U.S. Application Data

(60) Provisional application No. 61/898,162, filed on Oct. 31, 2013.

(51) Int. Cl.
| | |
|---|---|
| *G01N 33/53* | (2006.01) |
| *C12Q 1/34* | (2006.01) |
| *C12N 9/14* | (2006.01) |
| *C12Q 1/18* | (2006.01) |
| *G01N 33/542* | (2006.01) |

(52) U.S. Cl.
CPC ............... *C12Q 1/34* (2013.01); *C12N 9/14* (2013.01); *C12Q 1/18* (2013.01); *G01N 33/542* (2013.01); *C12Y 306/05003* (2013.01); *G01N 2500/02* (2013.01)

(58) Field of Classification Search
USPC .......... 435/6.1, 6.11, 7.1, 91.1, 183; 436/94, 436/501; 536/23.1, 24.3; 530/300, 350
See application file for complete search history.

(56) References Cited

U.S. PATENT DOCUMENTS

2014/0127681 A1*  5/2014  Blanchard ............ C07K 14/47
                                                          435/6.1

OTHER PUBLICATIONS

The definition of "antimicrobial" from Wikipedia, the free encyclopedia. Printed on Dec. 4, 2016.*
Perla-Kajan et al., Properties of *Escherichia coli* EF-Tu mutants designed for fluorescence resonance energy transfer from tRNA molecules. Protein Engineering Design & Selection, 23, 129-136, 2010.*
Laurentiis et al., Construction of a fully active Cys-less elongation factor Tu: Functional role of conserved cysteine 81. Biochimica et Biophysica Acta, 1814, 684-692, 2011.*

* cited by examiner

*Primary Examiner* — Frank W Lu
(74) *Attorney, Agent, or Firm* — Moser Taboada

(57) ABSTRACT

The present invention provides a novel assay that allows high-throughput screening of chemical compounds for the inhibition of binding between EF-Tu and tRNA.

12 Claims, 14 Drawing Sheets

Specification includes a Sequence Listing.

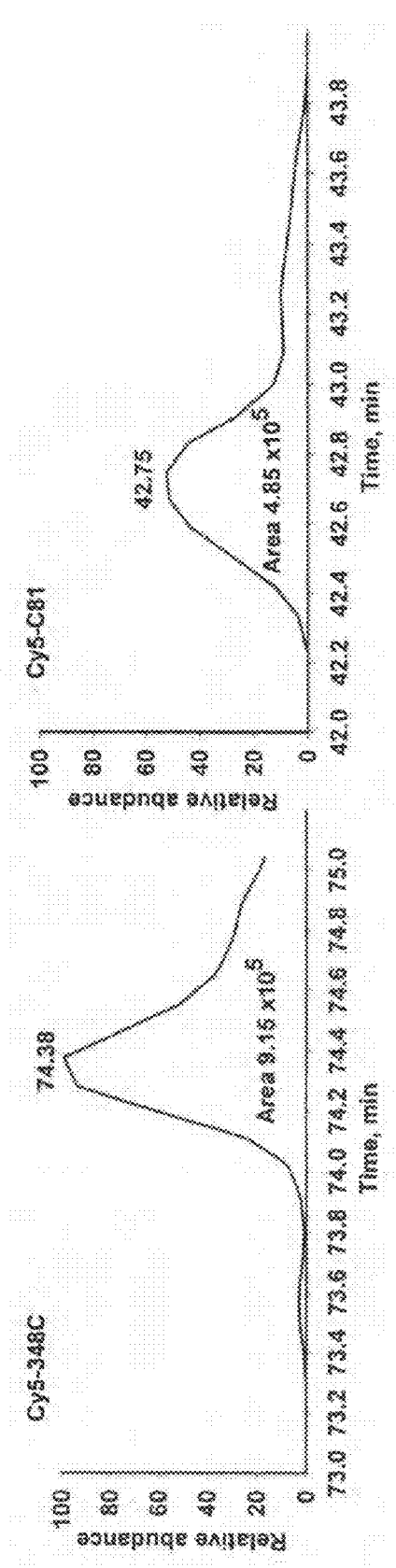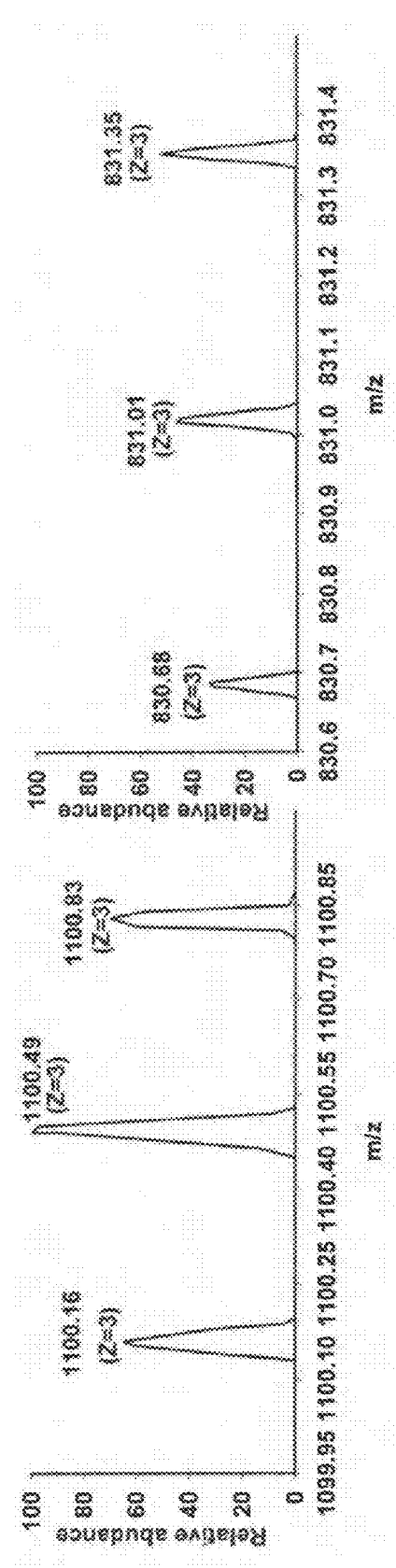
Figure 5A, Figure 5B, Figure 5C, Figure 5D

```
                          SEQUENCE LISTING

<160> NUMBER OF SEQ ID NOS: 3

<210> SEQ ID NO 1
<211> LENGTH: 393
<212> TYPE: PRT
<213> ORGANISM: Escherichia coli

<400> SEQUENCE: 1

Ser Lys Glu Lys Phe Glu Arg Thr Lys Pro His Val Asn Val Gly Thr
 1               5                  10                  15

Ile Gly His Val Asp His Gly Lys Thr Thr Leu Thr Ala Ala Ile Thr
                20                  25                  30

Thr Val Leu Ala Lys Thr Tyr Gly Gly Ala Ala Arg Ala Phe Asp Gln
             35                  40                  45

Ile Asp Asn Ala Pro Glu Glu Lys Ala Arg Gly Ile Thr Ile Asn Thr
 50                  55                  60

Ser His Val Glu Tyr Asp Thr Pro Thr Arg His Tyr Ala His Val Asp
 65                  70                  75                  80

Cys Pro Gly His Ala Asp Tyr Val Lys Asn Met Ile Thr Gly Ala Ala
                 85                  90                  95

Gln Met Asp Gly Ala Ile Leu Val Val Ala Ala Thr Asp Gly Pro Met
                100                 105                 110

Pro Gln Thr Arg Glu His Ile Leu Leu Gly Arg Gln Val Gly Val Pro
             115                 120                 125

Tyr Ile Ile Val Phe Leu Asn Lys Cys Asp Met Val Asp Asp Glu Glu
130                 135                 140

Leu Leu Glu Leu Val Glu Met Glu Val Arg Glu Leu Leu Ser Gln Tyr
145                 150                 155                 160

Asp Phe Pro Gly Asp Asp Thr Pro Ile Val Arg Gly Ser Ala Leu Lys
                165                 170                 175

Ala Leu Glu Gly Asp Ala Glu Trp Glu Ala Lys Ile Leu Glu Leu Ala
                180                 185                 190

Gly Phe Leu Asp Ser Tyr Ile Pro Glu Pro Glu Arg Ala Ile Asp Lys
            195                 200                 205

Pro Phe Leu Leu Pro Ile Glu Asp Val Phe Ser Ile Ser Gly Arg Gly
    210                 215                 220

Thr Val Val Thr Gly Arg Val Glu Arg Gly Ile Ile Lys Val Gly Glu
225                 230                 235                 240

Glu Val Glu Ile Val Gly Ile Lys Glu Thr Gln Lys Ser Thr Cys Thr
                245                 250                 255

Gly Val Glu Met Phe Arg Lys Leu Leu Asp Glu Gly Arg Ala Gly Glu
                260                 265                 270

Asn Val Gly Val Leu Leu Arg Gly Ile Lys Arg Glu Glu Ile Glu Arg
            275                 280                 285

Gly Gln Val Leu Ala Lys Pro Gly Thr Ile Lys Pro His Thr Lys Phe
    290                 295                 300

Glu Ser Glu Val Tyr Ile Leu Ser Lys Asp Glu Gly Gly Arg His Thr
305                 310                 315                 320

Pro Phe Phe Lys Gly Tyr Arg Pro Gln Phe Tyr Phe Arg Thr Thr Asp
                325                 330                 335

Val Thr Gly Thr Ile Glu Leu Pro Glu Gly Val Glu Met Val Met Pro
```

```
                    340                 345                 350
Gly Asp Asn Ile Lys Met Val Val Thr Leu Ile His Pro Ile Ala Met
            355                 360                 365

Asp Asp Gly Leu Arg Phe Ala Ile Arg Glu Gly Gly Arg Thr Val Gly
        370                 375                 380

Ala Gly Val Val Ala Lys Val Leu Ser
385                 390

<210> SEQ ID NO 2
<211> LENGTH: 15
<212> TYPE: PRT
<213> ORGANISM: Artificial Sequence
<220> FEATURE:
<223> OTHER INFORMATION: Synthetic peptide

<400> SEQUENCE: 2

His Tyr Ala His Val Asp Cys Pro Gly His Ala Asp Tyr Val Lys
 1               5                  10                  15

<210> SEQ ID NO 3
<211> LENGTH: 24
<212> TYPE: PRT
<213> ORGANISM: Artificial Sequence
<220> FEATURE:
<223> OTHER INFORMATION: Synthetic peptide

<400> SEQUENCE: 3

Thr Thr Asp Val Thr Gly Thr Ile Glu Leu Pro Glu Gly Val Cys Met
 1               5                  10                  15

Val Met Pro Gly Asp Asn Ile Lys
                20
```

ASSAY FOR IDENTIFICATION OF THERAPEUTICS TARGETING TERNARY COMPLEX FORMATION IN PROTEIN SYNTHESIS

This application claims priority under 35 U.S.C. § 119(e) to U.S. Provisional Patent Application No. 61/898,162, filed on Oct. 31, 2013. The foregoing application is incorporated by reference herein.

This invention was made with government support under Grant Number HG004364 awarded by the National Institutes of Health. The government has certain rights in the invention.

FIELD OF THE INVENTION

The present invention relates to a novel assay that allows high-throughput screening of compounds for the inhibition of binding between EF-Tu and tRNA. The identified compound(s) will inhibit function of an organism's protein synthesis machinery by blocking the activity of a required ternary complex that includes the molecules EF-Tu, tRNA, and GTP. As such, the compound(s) will inhibit protein biosynthesis in infectious microorganisms.

BACKGROUND OF THE INVENTION

Several publications and patent documents are cited throughout the specification in order to describe the state of the art to which this invention pertains. Each of these citations is incorporated herein by reference as though set forth in full.

Many bacterial diseases have become more deadly as bacteria have developed resistance to treatment with antibiotics. About half of all antibiotics target bacterial protein synthesis, but there are no inhibitors currently in use in clinical practice that target ternary complex formation (aminoacyl-tRNA, EF-Tu, and GTP). There are a few known naturally occurring inhibitors of this step that work in vitro (e.g., kirromycin and others), but these are not effective against gram-negative bacteria because they do not enter bacterial cells. Accordingly, there is a strong need to identify compounds for use as new antibiotics, including those which target the ternary complex.

SUMMARY OF THE INVENTION

In accordance with the instant invention, methods for detecting modulators (e.g., inhibitors) of the formation of the ternary complex are provided. Inhibitors of the formation of the ternary complex are antimicrobial compounds. In a particular embodiment, the method comprises mixing an elongation factor Tu (EF-Tu) with GTP and an aminoacylated transfer RNA (aa-tRNA) in the presence of a test compound, wherein the EF-Tu is operably linked to a first energy transfer pair member and the aa-tRNA is operably linked to a second energy transfer pair member, wherein said first energy transfer pair member and said second energy transfer pair member form a fluorescence resonance energy transfer pair. The fluorescence emitted by the sample is then detected/measured (qualitatively and/or quantitatively) and compared to the fluorescence observed in the absence of the test compound and/or the fluorescence observed in the presence of a control compound (e.g., a known inhibitor). A change in fluorescence from that observed in the absence of the test compound (or the observation of fluorescence similar to that observed in the presence of a known inhibitor) indicates that the test compound can inhibit formation of the ternary complex and possesses antimicrobial activity. In a particular embodiment, the EF-Tu comprises a non-cysteine residue at position 137, a non-cysteine residue at position 255, and a cysteine at position 348.

In accordance with another aspect of the instant invention, a variant EF-Tu is provided, which allows for attachment of a fluorophore. In a particular, the EF-Tu protein comprises a non-cysteine residue at position 137, a non-cysteine residue at position 255, and a cysteine at position 348. In a particular embodiment, the EF-Tu comprises the following three substitutions: C137A, C255V, and E348C.

BRIEF DESCRIPTIONS OF THE DRAWING

FIG. 1 shows the results of functional assays of mutant EF-Tu proteins. Non-enzymatic hydrolysis of Phe-tRNA$^{Phe}$ in the presence of *Escherichia coli* wild type or mutant EF-Tu proteins is shown. Each reaction contained 2.5 mM EF-Tu and 0.5 mM [$^{14}$C] Phe-tRNA$^{Phe}$.

FIG. 2 provides a schematic structure of the ternary complex. The sites chosen for labeling of the recombinant *Escherichia coli* EF-Tu mutants and tRNA$^{Phe}$ with Cy5 and Cy3, respectively, are shown. A cysteine residue was introduced at position 348 in EF-Tu. The distance between the Cy5-labeled cysteine residue and Cy3-labeled U47 on tRNA$^{Phe}$ is indicated. The coordinates for the *E. coli* EF-Tu:GDPNP:kirromycin:Phe-tRNA$^{Phe}$ ternary complex at 3.3 Å resolution are from the 1ob2 PDB file (Kavaliauskas et al. (2012) Biochemistry, 51:2642-2651). WebLab ViewerPro software was used to create the image.

FIGS. 3A and 3B show the purification of tRNA using reverse phase HPLC on the C4 Delta Pack column. The dashed lines represent an optimized buffer B gradient, with the % buffer B indicated by the scale on the right axis. FIG. 3A shows the separation of tRNA$^{Phe}$ and tRNA$^{Phe}$(Cy3). After the labeling reaction, the pool of tRNA$^{Phe}$ (4.75 A$_{260}$ units) was resolved using the conditions described herein. FIG. 3B shows the isolation of aminoacylated Cy3-labeled tRNA$^{Phe}$. The phenol-extracted and ethanol-precipitated aliquot of 5 A$_{260}$ units of *E. coli* tRNA$^{Phe}$(Cy3) after aminoacylation reaction with $^{14}$C Phe was applied to the C4 Delta Pack column. The retention time was 33 and 28 minutes for charged Phe-tRNA$^{Phe}$(Cy3) and uncharged tRNA$^{Phe}$(Cy3), respectively. Fractions containing tRNA$^{Phe}$(Cy3) and [$^{14}$C] Phe-tRNA$^{Phe}$(Cy3) were collected and ethanol-precipitated. A large peak (>1600 RU A$_{260}$) at the void volume was observed after the phenol extraction. The peak likely originated from oxidized phenol derivatives.

FIGS. 4A and 4B show poly(Phe) synthesis using Phe-tRNA$^{Phe}$(Cy3). For FIG. 4A, the reaction mixtures contained 20 mM magnesium acetate, 10 mM potassium phosphate, pH 7.4, 100 mM potassium glutamate, pH 7.7, 95 mM potassium chloride, 10 mM ammonium chloride, 0.5 mM calcium chloride, 1 mM spermidine, 8 mM putrescine, 1 mM DTT, 1 mM ATP, 4.5 mM PEP, 1 mM GTP, 100 µg/ml pyruvate kinase, 2 µM EF-G, 2 µM 70S ribosomes, 60 pmol [$^{14}$C] Phe-tRNA$^{Phe}$ or [$^{14}$C] Phe-tRNA$^{Phe}$(Cy3) and 30 pmol of *E. coli* EF-Tu. The reaction was carried out at 37° C. for 5 minutes, and then incubated with an equal volume of 0.4 M NaOH at 37° C. for 10 minutes. After hydrolysis of unreacted [$^{14}$C]Phe-tRNA$^{Phe}$ was completed, the sample was applied onto Whatman filter paper or GF filter, washed in 5% ice cold TCA and in ethanol. The radioactivity in the precipitates was determined by scintillation counting. For FIG. 4B, the reaction was carried out at the same conditions for 1 minute in two sets for [$^{14}$C] Phe-tRNA$^{Phe}$(Cy3) and

[$^{14}$C] Phe-tRNA$^{Phe}$. Concentrations of 70S ribosome and EF-Tu were 1 and 30 µM, correspondingly. The concentration of labeled and unlabeled aa-tRNA was in the 0.2-12.8 µM range.

FIGS. 5A, 5B, 5C, and 5D provide the LCMS-MS analysis of Cy5 maleimide-labeled EF-Tu (E348C mutant). Extracted ion chromatograms representing Cy5 modified Cys 348 (FIG. 5A), with m/z ratio 1100.1668 (FIG. 5B) and Cy5 modified Cys 81 (FIG. 5C), with m/z ratio 830.6873 (FIG. 5D). On base integration of EIC's peaks, the Cy5 dye distribution in EF-Tu is 65% at C348, and 35% at C81.

FIGS. 6A, 6B, 6C, and 6D provide gel retardation assays showing the monitoring of ternary complex formation by autoradiography. After electrophoresis, the gels were placed in a phosphorimager cassette and scanned after an overnight exposure. [$^{14}$C] Phe-tRNA$^{Phe}$(Cy3) (0.4 µM) was incubated in the presence of GTP and increasing concentrations of native EF-Tu (FIG. 6A), His-tagged recombinant wild-type EF-Tu (FIG. 6B), E348C(AV) mutant (FIG. 6C) or K324C (AV) mutant (FIG. 6D) were run on the gel as described. Each line contains 4 pmol of $^{14}$C Phe tRNA$^{Phe}$ (except 20 pmol in line 1, FIGS. 6A and 6B). The amount of EF-Tu was varied between 0.4-2.8 µM.

FIGS. 7A and 7B provide gel retardation assay to monitor ternary complex formation. After native gel electrophoresis, two gels were scanned to monitor Cy3 (left) or Cy5 (right) fluorescence. For FIG. 7A, each line contains 2 pmol of Phe-tRNA$^{Phe}$(Cy3). Unlabeled EF-Tu WT, E348C mutant or Cy5 EF-Tu WT were added in 8-fold molar excess (lines 2-4). Cy5 EF-Tu E348C concentration was varied in 1-8 molar excess (lines 5-8). Cy3 maleimide dye itself was loaded as a control for Cy3 fluorescence in line 9. The total Cy3 fluorescence intensity of labeled tRNA in the ternary complex with Cy5-EF-Tu E348C was decreased approx 27% (calculation is based on the band intensity in lines 1 and 2 vs. lines 5 and 6). The quenching of Cy3 fluorescence in the complex is close to 60% (calculation is based on the band intensity in lines 2 and 4 vs. lines 5 and 6). For FIG. 7B, Phe-tRNA$^{Phe}$(Cy3) (0.2 µM) was incubated with four-fold molar excess of Cy5 EF-Tu WT or Cy 5 E348C. No ternary complex was observed in presence of EDTA (line 4) as well as in presence of uncharged tRNAµ (Cy3) (lines 5, 6 and 7). The total Cy3 fluorescence intensity of the labeled tRNA in the ternary complex with Cy5-EF-Tu E348C was decreased approx 24% (calculation is based on the band intensity in line 1 vs. line 3). Quenching of Cy3 fluorescence in the complex is close to 60% —calculation is based on the intensity of the ternary complex band in line 2 (peak 1) and line 3 (peak 4). Approximately 46% of Phe-tRNA$^{Phe}$(Cy3) was deacylated after the reaction. The band intensity was calculated using the ImageQuant software.

For FIGS. 8A and 8B, spectral (FIG. 8A) and time-based (FIG. 8B) evidence of fluorescent resonance energy transfer (FRET) upon addition of Phe-tRNA$^{Phe}$(Cy3) to Cy5 EF-Tu E348C in presence of GTP is shown. For FIG. 8A, the ternary complex was formed in a 24 µl volume using Phe-tRNA$^{Phe}$(Cy3) [0.2 µM], GTP [100 µM], Cy5-EF-Tu WT or E348C [0.4 µM]. The conditions and incubation buffer are as described for the gel retardation assay. A 12-µl volume was loaded on a native 10% polyacrylamide gel (insert), and remaining volume was adjusted to 140 The Cy3 fluorescence was monitored on a Photon Technology International fluorescence spectrofluorometer in the spectrum mode at excitation/emission 549/565 nm. For FIG. 8B, a time-base titration experiment was carried out in a 150 ml black cuvette at RT. Phe-tRNA$^{Phe}$(Cy3) [60 nM] was in the incubation buffer supplemented with 1 mM ATP and 5 µg/ml of Phe-tRNA synthetase. Cy3 fluorescence (excitation/emission 549/565 nm) was monitored at five sec interval up to 1 hour. Cy5 EF-Tu E348C was added from concentrated stock solution to reach final concentration[180 nM]. The 70s ribosome concentration was [240 nM] and poly(U) was 64 µg/ml.

FIG. 9 shows the effect of aminoacylation of tRNA$^{Phe}$ (Cy3) on FRET during ternary complex formation. Cy5-labeled EF-Tu [320 nM] (GTP form) in a 300-µl volume was placed in 1× incubation buffer. The reaction was supplemented with 100 µM GTP and split into two parts. The FRET upon formation of ternary complex was monitored at 665 nm (suitable for the Cy5 dye) in the time-base mode using the 532 nm excitation for the Cy3 dye. Plot 1 indicates a 4.7-fold increase in Cy5 fluorescence upon addition (10 min) of Phe-tRNA$^{Phe}$(Cy3). Plot 2: an addition of the same amount of the uncharged tRNA$^{Phe}$(Cy3) minimally affects the Cy5 fluorescence due to absence of FRET (see inset).

FIG. 10 shows the titration of GTP:Cy5-E348C by Phe-tRNA$^{Phe}$(Cy3) and displacement of labeled EF-Tu from the ternary complex by the unlabeled form. Cy5-labeled EF-Tu [360 nM] (GTP form) in a 300 µl volume was placed in 1× incubation buffer supplemented with 100 µM GTP. The Cy5 fluorescence was monitored for 5 mM at 25° C. using the 532 nm excitation wavelength. After addition of Phe-tRNA$^{Phe}$(Cy3), the concentration was increased step-wise in the 90-540 nM range, and fluorescence was monitored at 10-min intervals. After the saturation point was reached (1 hour), a 10-fold molar excess of unlabeled EF-Tu E348C was added to the cuvette, and the fluorescence was monitored for one additional hour. The inset shows differences in Cy5 fluorescence of Cy5-EF-Tu E348C excited directly at either 532 nm (bottom line) or 633 nm (top line) wavelength.

FIGS. 11A and 11B show EF-Tu fluorescence in ternary complex. For FIG. 11A, the relative fluorescence F/Fo plotted against the concentration of elongation factor Tu in titration of GTP: Cy5-E348C by Phe-tRNA$^{Phe}$(Cy3) is shown. For FIG. 11B, normalized fluorescence intensity upon displacement of labeled form EF-Tu from the ternary complex in the presence of 10 molar excess of unlabeled EF-Tu is shown.

FIG. 12 shows the displacement of GTP:EF-Tu from ternary complex by GDP. Cy5-labeled EF-Tu [180 nM] (GTP form) in a 300-ml volume was placed in 1× incubation buffer. The reaction volume was split into two parts, and was supplemented with 100 µM GTP (plot 1, top line) or GDP (plot 2, bottom line) and incubated at 25° C. with monitoring of Cy5 fluorescence. The GTP:Cy5-labeled EF-Tu (I) shows approximately 4-fold increase in the Cy5 fluorescence upon an addition of Phe-tRNA$^{Phe}$(Cy3) [160 nM] (addition made after 5 min incubation, arrow). An addition of 10-fold molar excess of GDP led to a 60% decrease in the Cy5 fluorescence. When the Cy5-labeled EF-Tu was incubated with GDP (plot 2), the FRET response also was significantly lower.

DETAILED DESCRIPTION OF THE INVENTION

Figure 1:
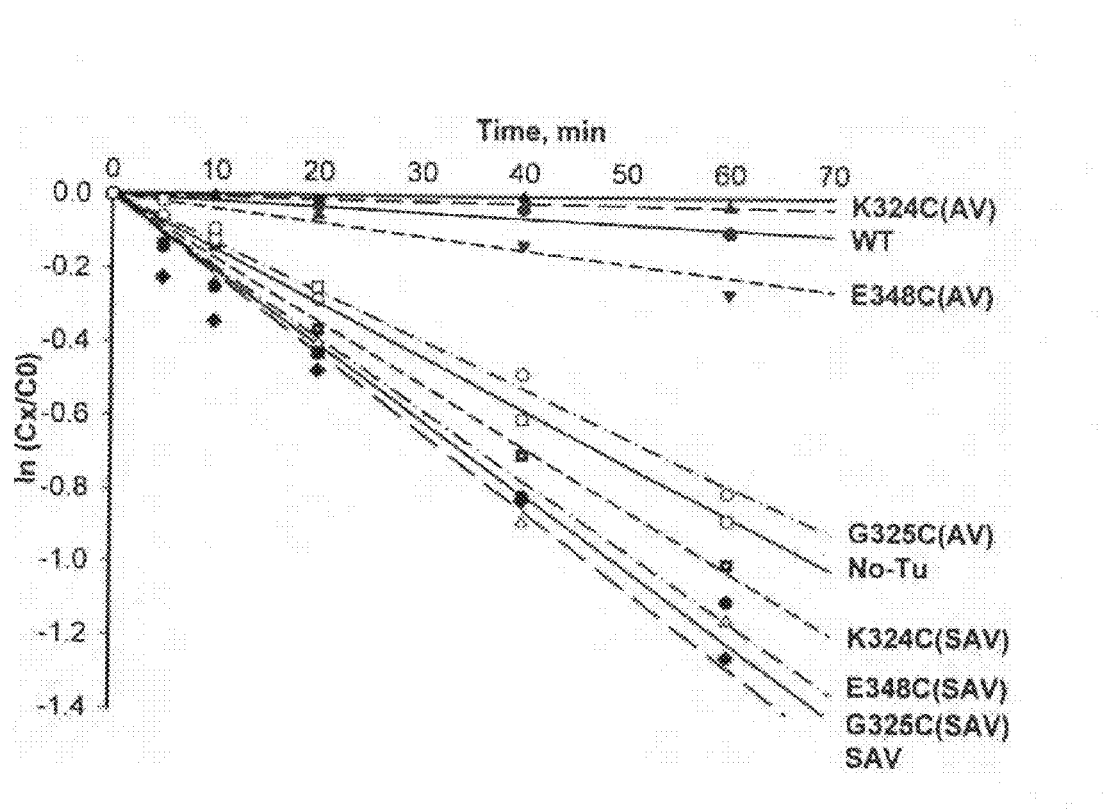

Formation of the ternary complex between GTP-bound form of elongation factor Tu (EF-Tu) and aminoacylated transfer RNA (aa-tRNA) is a key event in protein biosynthesis. Herein, it is shown that fluorescently modified *Escherichia coli* EF-Tu carrying three mutations, C137A, C255V and E348C, and fluorescently modified Phe-tRNA$^{Phe}$ form functionally active ternary complex that has properties similar to those of the naturally occurring (unmodified) complex. Similarities include binding and binding rate constants, behavior in gel retardation assay, as well as activities in tRNA protection and in vitro translation assays. Proper labeling of EF-Tu was demonstrated in MALDI mass spectroscopy experiments. To generate the mutant EF-Tu, a series of genetic constructions were performed. Two native cysteine residues in the wild-type EF-Tu at positions 137 and 255 were replaced by Ala and Val, respectively, and an additional cysteine was introduced either in position 324 or 348. The assembly FRET assay showed a 5- to 7-fold increase of Cy5-labeled EF-Tu E348C mutant fluorescence upon formation of ternary complex with charged tRNA$^{Phe}$ (Cy3-labeled) when the complex was excited at 532 nm and monitored at 665 nm. In a control experiment, FRET was not observed using uncharged tRNA$^{Phe}$(Cy3), nor with wild-type EF-Tu preparation that was allowed to react with Cy5 maleimide, nor in the absence of GTP. The results obtained demonstrate that the EF-Tu:tRNA FRET system described can be used for investigations of ribosomal translation in many types of experiments.

Using advanced protein engineering, EF-Tu has been modified to accept attachment of fluorescent dyes while retaining normal function. Using this modified EF-Tu along with a fluorescently-tagged tRNA molecule, fluorescence resonance energy transfer (FRET) has been demonstrated upon formation of the ternary complex. The modified molecules were shown to be capable of carrying out their function in protein synthesis normally. These reagents are thus a powerful tool for rapid screening of a library of compounds (e.g., small molecules) to determine their ability to inhibit ternary complex formation by preventing FRET from being observed.

Because ternary complex formation between EF-Tu and tRNA is a universal requisite for protein synthesis, antibiotics identified by the methods of this invention can have broad specificity against gram-negative bacteria as well as gram-positive bacteria (e.g., *Staphylococcus*) and tuberculosis infections. Although human cells also require ternary complex formation, the human versions of these molecules are sufficiently different from bacterial forms that compounds that affect bacteria ternary complex formation are unlikely to inhibit mammalian ternary complex formation. Indeed, many inhibitors of bacterial protein synthesis do not inhibit human protein synthesis.

EF-Tu is an ideal target for the development of novel antibacterial agents because the protein is essential and highly conserved among bacteria. Among enteric pathogens that could be treated by the compounds identified by the methods of the instant invention include, without limitation, *E. coli* O157:H7, other enterotoxigenic *E. coli* (ETEC), *Shigella*, *Vibrio cholerae*, *Klebsiella pneumoniae*, and others. Increased antibiotic resistance has threatened the ability to treat diseases caused by these bacteria. This has become a critical concern with the recent emergence of resistance to antibiotics of last resort, carbapenems. "Superbugs" carrying this resistance are also resistant to almost all known antibiotics in clinical use and are a significant threat to global health. Accordingly, there is urgent need to develop new antibiotics.

The method of the instant invention allows for an identification of antibiotics for treating, inhibiting, and/or preventing bacterial infections and/or the diseases or disorders associated therewith. The identified chemical compound will inhibit the binding of key components of ribosomal translation machinery in the cell and, therefore, will inhibit protein biosynthesis in the infectious microorganism.

The instant invention provides assays and methods for the identification of a new class of antibiotics that will provide new protection from dangerous diseases and will directly impact therapies. The present invention demonstrates an assay suitable for high-throughput screening of compounds (e.g., a chemical library) for the inhibition of the formation of the ternary complex, particularly binding between EF-Tu and tRNA. The inhibitory effect in this assay is demonstrated using two compounds known to affect the binding (kirromycin and GDP). In a control experiment, it was shown that an unmodified form of tRNA does not support the assay.

As stated hereinabove, the assay of the instant invention involves two key biological molecules in ribosomal translation, tRNA and EF-Tu. A variant of *Escherichia coli* EF-Tu which can be used in the assay has been designed specifically through advanced protein engineering. The modified EF-Tu carries three mutations which allow for site-directed fluorescence labeling of the protein while still retaining full function in protein synthesis. As example, the assay comprises two main reagents: Cy5-labeled EF-Tu from an engineered *E. coli* mutant [C137A, C255V, E348C] and Cy3-labeled Phe-tRNA$^{Phe}$ of *E. coli*. The naturally occurring nucleotide 3-(3-amino-3-carboxy-propyl)uridine (acp$^3$U) at position 47 of tRNA$^{Phe}$ from *E. coli* was chosen for labeling. The modification does not change the biological properties of this tRNA, and the modified tRNA has been used in many successful translation experiments. Both Cy5 and Cy3 are fluorescent dyes. If labeled tRNA binds labeled EF-Tu, both dyes are in proximity (less than 30 Å). When the biomolecular complex is illuminated with laser light at the wavelength at which Cy3 is excited (530 nm), fluorescence resonance energy transfer (FRET) is observed. As a result, Cy5-labeled EF-Tu emits light at 670 nm and the amount of light is proportional to the concentration of the tRNA-EF-Tu complex. An inhibitor will disrupt the binding and result in a lower fluorescence intensity observed at 670 nm. This allows for the identification of the inhibitor. This type of bioassay is known as a homogeneous assay. It is the type favored in high-throughput screening since running an assay can be as simple as mixing the reagents (tRNA and EF-Tu) and the chemical compound being tested, followed by reading out the fluorescence intensity. Because EF-Tu is chemically different than its human homolog (eEF1a), selectivity that will target the bacterial protein and not the human homolog can be obtained.

Drug discovery projects, similarly to the described invention, are often based on identifying a molecular target in an in vitro assay and performing a high-throughput screen of a library of chemical compounds. The identified inhibitor is an effective antibiotic which may be modified through medicinal chemistry to optimize the chemical structure of the compound for stability, delivery, and efficacy. Pharmaceutical companies are always looking for new antibiotics, especially because of the increase in resistance to current antibiotics found in many pathogens. This invention targets an aspect of bacterial metabolism that has largely been unexploited for development of antibiotics. Further, because EF-Tu has to interact with a large number of molecules (40 or more different tRNAs, and proteins including EF-Ts and ribosomal proteins), it will be difficult for pathogens to develop resistance to a drug that targets EF-Tu. This sensitive and specific assay for the interaction of EF-Tu with tRNA provides an excellent way to target this interaction.

In accordance with the instant invention, methods of screening for antibiotic activity are provided. The agents to be screened by the methods of the instant invention can be any compound (e.g., an isolated compound), particularly any natural or synthetic chemical compound (such as a small molecule, including a combinatorial chemistry library of small molecules), organic compounds and molecules, inorganic compounds and molecules (e.g., heavy metal containing compounds), biological macromolecules (e.g., saccharides, lipids, peptides, proteins, polypeptides and nucleic acid molecules (e.g., those encoding a protein of interest)), inhibitory nucleic acid molecule (e.g., antisense or siRNA), and drugs (e.g., an FDA approved drug). In a particular embodiment, small molecules are screened using the method of the instant invention.

The present invention provides methods for screening for compounds/agents that can inhibit the formation of the ternary complex, thereby indicating the compound/agent is an antimicrobial (e.g., an antibiotic). In these methods, a modified EF-Tu will be mixed (e.g., brought into proximity) with GTP and an aminoacylated transfer RNA (aa-tRNA) and, optionally, one or more test compounds. This mixing will take place under appropriate conditions for the formation of the ternary complex. Any alteration or difference (e.g., a reduction) in the level of fluorescence detected in the presence of the one or more test compounds, as compared with the level of fluorescence detected in the absence of the test compound(s), will be an indication that the test compound(s) is capable of modulating (e.g., inhibiting) the formation of the ternary complex.

To produce the FRET of the instant invention, the EF-Tu and the aa-tRNA are each attached to at least one energy transfer pair member so as to form an energy transfer pair. In a particular embodiment, EF-Tu is labeled with a fluorescent group and the aa-tRNA is labeled with a matching/corresponding quenching/fluorescent group. In a particular embodiment, the fluorescent group is attached to aa-tRNA and the matching/corresponding quencher/fluorescent group is attached to the EF-Tu. In a particular embodiment, the matching/corresponding quenching/fluorescent group absorbs the energy emitted by the fluorescent group and emits the energy at a different wavelength. Under such a set-up, the emission from the quenching/fluorescent group is observed when the ternary complex is formed and not when complex formation is blocked by an inhibitor. In a particular embodiment, the matching/corresponding quenching/fluorescent group absorbs the energy emitted by the fluorescent group (e.g., it is a quencher of the energy emitted by the first fluorescent group). Under such a set-up, the emission from the fluorescent group is not observed when the ternary complex is formed, but is observed when complex formation is blocked by an inhibitor as the energy transfer pair members are too distant.

The EF-Tu and the aa-tRNA may have the energy transfer pair member attached at a single, specific site. This may be achieved, for example, by mutation of a single residue in the protein to a cysteine residue, which allows for thiol specific chemistry to add the energy transfer pair member. As explained herein, care should be taken with the placement of the energy transfer pair members on the proteins to avoid negatively impacting their activity and/or ability to form the ternary complex.

As stated hereinabove, methods of the present invention are amenable to high-throughput screening formats because the use of fluorescence and FRET based assays is a standard platform known in the art for HTS. In a particular embodiment, the formation of the ternary complex of the instant invention is performed within a microarray (e.g., in a microassay plate). Such microarrays allow for researchers to quickly and cost effectively screen numerous inhibitors (e.g., a library) at the same time.

The present invention also provides kits for screening for inhibitors. In some embodiments, the kits comprise each of modified EF-Tu, GTP, and an aminoacylated transfer RNA as described hereinabove. In a particular embodiment, the components are maintained in different compositions (e.g., with at least one carrier). Instructions may be included which explain how to conduct the assay, how to detect fluorescence, and/or how to correlate fluorescence to inhibitor activity. Other optional reagents in the kit can include appropriate buffers for performing the assay.

In a particular embodiment of the instant invention, the EF-Tu is a variant of the wild-type *E. coli* EF-Tu. In a particular embodiment, the EF-Tu variant comprises a cysteine at position 348. The EF-Tu variant may further comprise a non-cysteine residue at position 137 and a non-cysteine residue at position 255. In a particular embodiment, the EF-Tu variant comprises the following three substitutions: C137A, C255V, and E348C. The amino acid sequence of wild-type *E. coli* EF-Tu is provided at GenBank Accession No. NP_418407 and GeneID: 948482. An exemplary amino acid sequence of *E. coli* EF-Tu is:

```
                                                        (SEQ ID NO: 1)
  1  SKEKFERTKP HVNVGTIGHV DHGKTTLTAA ITTVLAKTYG GAARAFDQID

51  NAPEEKARGI TINTSHVEYD TPTRHYAHVD CPGHADYVKN MITGAAQMDG

101  AILVVAATDG PMPQTREHIL LGRQVGVPYI IVFLNKCDMV DDEELLELVE

151  MEVRELLSQY DFPGDDTPIV RGSALKALEG DAEWEAKILE LAGFLDSYIP

201  EPERAIDKPF LLPIEDVFSI SGRGTVVTGR VERGIIKVGE EVEIVGIKET

251  QKSTCTGVEM FRKLLDEGRA GENVGVLLRG IKREEIERGQ VLAKPGTIKP

301  HTKFESEVYI LSKDEGGRHT PFFKGYRPQF YFRTTDVTGT IELPEGVEMV

351  MPGDNIKMVV TLIHPIAMDD GLRFAIREGG RTVGAGVVAK VLS.
```

While the EF-Tu of the instant invention is exemplified as from *E. coli*, the EF-Tu from other organisms or other bacteria may be used. In particular embodiments, the EF-Tu molecule has at least 75%, 80%, 85%, or more particularly, at least 90%, 95%, 97%, or 99% homology with SEQ ID NO: 1.

Any energy transfer pair can be used with the substrates and methods of the invention. Energy transfer pairs are known in the art. Examples of acceptable fluorphores include, without limitation, fluorescein, tetramethylaminorhodamine (TAMRA), 5-FAM (5-Carboxyfluorescein), tetrachloro-6-carboxyfluorescein (TET), 2,7-dimethoxy-4,5-dichloro-6-carboxyfluoroscein (JOE), hexachlorofluorescein (HEX), Oregon Green®, Alexa Fluor®, ROX, Cy3, Cy3.5, CAL Red™, Red 640, Cy5, and Cy5.5. Quenchers include, without limitation, QXL™ or BHQ™ quenchers. In a particular embodiment, the FRET pair is Cy5 and Cy3.

Definitions

The following definitions are provided to facilitate an understanding of the present invention:

The singular forms "a," "an," and "the" include plural referents unless the context clearly dictates otherwise.

As used herein, the term "small molecule" refers to a substance or compound that has a relatively low molecular weight (e.g., less than 4,000 atomic mass units (a.m.u.), particularly less than 2,000 a.m.u.). Typically, small molecules are organic, but are not proteins, polypeptides, or nucleic acids, though they may be amino acids or dipeptides.

The term "isolated" may refer to a compound or complex that has been sufficiently separated from other compounds with which it would naturally be associated. "Isolated" is not meant to exclude artificial or synthetic mixtures from other compounds or materials, or the presence of impurities that do not interfere with fundamental activity or ensuing assays, and that may be present, for example, due to incomplete purification, or the addition of stabilizers.

"Nucleic acid" or a "nucleic acid molecule" as used herein refers to any DNA or RNA molecule, either single or double stranded and, if single stranded, the molecule of its complementary sequence in either linear or circular form.

"Antisense molecule" refers to a nucleic acid molecule that hybridizes to all or a portion of a target gene or all or a portion of an mRNA encoded by a target gene. Such antisense molecules are typically between 15 and 30 nucleotides in length and often span the translational start site of mRNA molecules.

"Small interfering RNA" (siRNA) refers to an RNA comprising between about 10-50 nucleotides which is capable of directing or mediating RNA interference. Typically, siRNA molecules are double stranded RNA molecules between about 15 and 30 nucleotides in length, particularly 18-25 nucleotides in length, particularly about 21 nucleotides in length. The nucleotide sequence of the siRNA molecules commonly begin from an AA dinucleotide sequence.

The term "treat" as used herein refers to any type of treatment that imparts a benefit to a patient afflicted with a disease or disorder or infection, including improvement in the condition of the patient (e.g., in one or more symptoms), delay in the progression of the condition, etc.

As used herein, the term "prevent" refers to the prophylactic treatment of a subject who is at risk of developing a condition (e.g., bacterial infection) resulting in a decrease in the probability that the subject will develop the condition.

A "therapeutically effective amount" of a compound or a pharmaceutical composition refers to an amount effective to prevent, inhibit, or treat a particular disorder or disease and/or the symptoms thereof. For example, "therapeutically effective amount" may refer to an amount sufficient to modulate stress and/or stress response in a subject.

As used herein, the term "subject" refers to an animal, particularly a mammal, particularly a human.

As used herein, the phrases "fluorescence resonance energy transfer" and "FRET" refer to the energy transfer from an excited fluorescent group to, at least partially, a quenching/fluorescent group. The quenching/fluorescent group may radiate the absorbed light as light of a different wavelength or dissipate it as heat. FRET depends on 1) an overlap between the emission spectrum of the fluorescent group and the absorption spectrum of the quenching/fluorescent group and 2) the distance between the quenching/fluorescent group and the fluorescent group. Above a certain critical distance, the quenching/fluorescent group is unable to absorb the light emitted by the fluorescent group.

As used herein, the term "fluorescent group" (sometimes referred to as a fluorophore or FRET donor) refers to a molecule that, when excited with light having a selected wavelength, emits light of a different wavelength. A quenching/fluorescent group refers to a group that can absorb at least partly the energy/light emitted by a fluorescent group. Depending on the identity of the quenching/fluorescent group, the fluorescence emission can undergo a number of alterations, including, but not limited to, attenuation, complete quenching, a shift in wavelength, a shift in polarity, and a change in fluorescence lifetime. For example, the quenching/fluorescent group may radiate the absorbed light as light of a different wavelength.

As used herein, the term "energy transfer pair" refers to any two molecules that participate in fluorescence resonance energy transfer. The energy transfer pair is typically two molecules that participate in fluorescence resonance energy transfer. The energy transfer pair may comprise a first energy transfer pair member and a second energy transfer pair member. Typically, the first energy transfer pair member is different than the second energy transfer pair member.

As used herein, the term "microarray" refers to an ordered arrangement of array elements. The array elements are arranged so that there are at least one or more different array elements. The array elements may be contained within/on a solid support and need not be immobilized on the solid support. For example, an array of substrates in solution may be contained in a microtiter plate. The phrase "solid support" refers to any solid surface including, without limitation, any chip (for example, silica-based, glass, or gold chip), glass slide, membrane, plate, bead, solid particle (for example, agarose, sepharose, polystyrene or magnetic bead), column (or column material), test tube, or microtiter dish/plate.

The term "operably linked" refers to a juxtaposition/linkage wherein the components so described are in a relationship permitting them to function in their intended manner.

The following examples are provided to illustrate various embodiments of the present invention. The examples are illustrative and are not intended to limit the invention in any way.

EXAMPLE 1

Elongation factor Tu (EF-Tu), an important component of the translation apparatus, represents up to 5% of total protein in the bacterial cell and has been the subject of intensive structural studies (Kavaliauskas et al. (2012) Biochemistry, 51:2642-2651). *Escherichia coli* EF-Tu is a 393-amino acid guanine nucleotide-binding protein organized as a three domain structure which undergoes distinct conformational changes upon formation of active (GTP-bound) or inactive (GDP-bound) states (Berchtold et al. (1993) Nature, 365: 126-132). The active form of EF-Tu is part of a ternary complex (EF-Tu:GTP:aa-tRNA), which brings aminoacyl-tRNA to the A site of ribosome during translation (reviewed by Schmeing et al. (2009) Nature, 461:1234-1242). Upon codon-anticodon recognition, the EF-Tu conformation changes, leading to GTP hydrolysis, dissociation of the GDP-bound inactive form from the ribosome, combined with the delivery of the cognate aa-tRNA into the A site. Importantly, GTPase activity of EF-Tu itself is 107-fold lower without the presence of a codon programmed ribosome (Pape et al. (1998) EMBO J., 17:7490-7497). Nucleotide exchange factor EF-Ts forms a complex with GDP-bound EF-Tu for regeneration of the active GTP form (Miller et al. (1974) Methods Enzymol., 30: 219-232; Gromadski et al. (2002) Biochemistry, 41:162-169) capable again of binding aa-tRNA with high affinity and forming ternary complex for delivery of the next amino acid into the growing polypeptide chain.

Single-molecule techniques are among the most powerful modern tools for investigation of the translation machinery in real time (Mandecki et al., 2008; Marshall et al., 2008). Progress in using smFRET (single molecule fluorescent resonance energy transfer) depends on many factors, including instrumentation setup, immobilization chemistry as well as successful labeling of target, i.e., biologically active macromolecules with appropriate fluorophores. Currently successful smFRET studies include chemical modification with fluorescent dyes of tRNA molecules ($tRNA^{Phe}$, $tRNA^{fMet}$, $tRNA^{Arg}$, $tRNA^{Lys}$) and ribosomal protein L11 (Uemura et al. (2010) Nature, 464:1012-1017; Bharill et al. (2011) ACS Nano., 5:399-407; Chen et al. (2011) Mol. Cell, 42:367-377), but so far no reports were made for elongation factor Tu. Recently, 10 EF-Tu mutants were generated for the purpose of using them in FRET studies, including possible application for collecting sequence data directly from mRNA transcripts using codon-programmed ribosomes (Perla-Kajan et al. (2010) Protein Eng. Des. Sel., 23:129-136). Properties of these mutants were carefully investigated for functional stability in different types of assays, and three of them, K324C, G325C and E348C, were chosen for further studies. In all the above-mentioned mutants, the native cysteine residues at positions C81, C137 and C255 were replaced by serine (S), alanine (A) and valine (V) residues, respectively, so this series of mutants was named EF-TuSAV (SAV background). Unfortunately, derivatives of EF-TuSAV showed diminished activity in protein synthesis and related assays. This can be understood in light of recent (De Laurentiis et al. (2011) Biochim. Biophys. Acta, 1814:684-692) and other data (Miller et al. (1971) Arch. Biochem. Biophys., 144:115-121; Arai et al. (1974) J. Biochem., 76:523-534) that showed the importance of cysteine 81 for aminoacyl-tRNA binding. In this study, the K324C, G325C and E348C mutations were moved into an AV background, where the native cysteine residue was retained at position 81 while the other two cysteine residues were replaced by Ala and Val, respectively. These mutants were fluorescently labeled and tested in a number of functional assays, including FRET studies, using commercially available or recombinant E. coli EF-Tu as a control. The results demonstrate that E348C mutant with AV background is an excellent compound for smFRET studies.

Materials and Methods

Reagents

Wild-type E. coli elongation factor Tu was from tRNA Probes LLC (USA). Construction of recombinant His-tagged EF-Tu was performed as described (Perla-Kajan et al. (2010) Protein Eng. Des. Sel., 23:129-136). E. coli $tRNA^{Phe}$ was purchased from Chemical Block (Moscow, Russia). The phenylalanine acceptor activity of tRNA was approximately 1000 pmol/$A_{260}$ unit. Synthetic peptide HYAHVDCPGHADYVK, corresponding EF-Tu sequence 75-89 was from GenScript, Inc. (USA). Cy3 N-hydroxysuccinimide ester (NHS) ester was from GE Healthcare or from Primetech LTD (Minsk, Belarus), Cy5 maleimide was from GE Healthcare. Sodium citrate-saturated phenol (pH 4.3), ammonium acetate, ammonium chloride, magnesium acetate, magnesium chloride, potassium chloride, sodium bicarbonate, DTT, ATP, GDP, GTP, GDPNP, TCEP, L-phenylalanine were from Sigma. L-[$^{14}$C] phenylalanine (476 mCi/mmol) was from PerkinElmer (Boston, Mass.).

Protein and Ribosome Preparation

Recombinant his-tagged E. coli EF-Tu and phenylalanine tRNA synthetase (PheRS) were expressed in E. coli BL-21 and XL-Blue strains, respectively, and purified on Ni-NTA columns as described (Perla-Kajan et al. (2010) Protein Eng. Des. Sel., 23:129-136) with minor modifications. In some cases, protein after Ni-NTA column was additionally purified by anion exchange chromatography on DEAE Toypearl 650 M. E. coli extracts and 70s ribosomes were prepared as described (Goldman et al. (1972) J. Mol. Biol., 67:35-47; Goldman et al. (1979) Methods Enzymol., 59:292-309).

Labeling of $tRNA^{Phe}$

The labeling reaction was as described (Plumbridge et al. (1980) Nucleic Acids Res., 8:827-843; Blechschmidt et al. (1994) Eur. J. Biochem., 219:65-71; Fei et al. (2008) Mol. Cell, 30:348-359) with minor modifications, and typically was carried out in a 100-μl volume by incubating up to 18 nM (4.54 mg/ml) of $tRNA^{Phe}$ with 0.52 μM (4 mg/ml) of Cy3 NHS ester in 0.1 M sodium bicarbonate buffer, pH 8.3, at room temperature for 5 hours, followed by an overnight incubation at 4° C. The reaction was stopped by addition of 1/10 volume of 3 M NaOAc, pH 5.5. An equal volume of sodium citrate-saturated phenol (pH 4.3) was added to the sample and the contents of the test tube were mixed thoroughly. The organic and aqueous phases were separated by centrifuging briefly at 18 000 g. Phenol extraction was repeated five times until the unreacted Cy3 dye was no longer seen in the organic phase. The aqueous phase was transferred to a new tube and extracted twice with chloroform. tRNA was precipitated by adding three volumes of ethanol, which was followed by an overnight at −20° C. (or 40 minutes at −80° C.). After centrifugation at 18 000 g for 20 minutes, the pellet was washed twice with 70% ethanol, briefly dried under vacuum, and dissolved in 50 ml of sterile water.

Aminoacylation of tRNA

The aminoacylation reaction was as described (Walker et al. (2008) Methods, 44:81-86; Perla-Kajan et al. (2010) Protein Eng. Des. Sel., 23:129-136) and carried out in 80 mM HEPES (pH 7.5), 8 mM $MgCl_2$, 24 mM KCl, 2 mM ATP, containing 100 μM [$^{14}$C]Phe (487 mCi/mmol) or 'cold' Phe, 10 μM $tRNA^{Phe}$(Cy3) and 7 μg/ml of recombinant Phe-tRNA synthetase. After 30 minutes of incubation at 37° C., the reaction mix was extracted once with phenol, twice with chloroform, and ethanol precipitated. The dried pellet was dissolved in sterile water. The preparation was stored at −80° C.

Reverse Phase High-Performance Liquid Chromatography

The RP high-performance liquid chromatography (HPLC) C4 Delta Pack column (3.9×300 mm, 15 mM, 300 A, Waters Corp., Japan) was used to separate the labeled tRNAs. The purification protocol was optimized for Beckman Coulter HPLC system. Buffer A contained 20 mM $NH_4OAc$ (pH 5.2), 10 mM MgOAc, 0.4 M NaCl, 3 mM $NaN_3$, and Buffer B had the same composition but was supplemented with 60% methanol (no sodium azide). The column was equilibrated for 20 minutes with Buffer A. Sample volume was 50 μl and contained up to 30 $A_{260}$ units of tRNA$^{Phe}$. The gradient 0-50% of Buffer B (run time 0-30 minutes) followed by 50-100% of Buffer A (run time 30-42 minutes) at flow rate of 0.5 ml/min was used for separation. Products were monitored at 260 nm for tRNA and 550 nm for the Cy3 dye and also by scintillation counting. After each purification cycle, the column was washed first with 10 column volumes of 100% Buffer B and then with 50% Buffer B. Fractions of interest were precipitated by isopropyl alcohol; the pellet was washed by 70% ethanol and dissolved in sterile water or 2 mM MgOAc, pH 5.2 and stored at −80° C.

UV/Vis Spectroscopy

UV/Vis spectra of labeled tRNA$^{Phe}$ and EF-Tu samples were monitored on Varian Cary 50 Bio and Nanodrop ND-1000 spectrophotometers using molar extinction coefficients $\varepsilon_{260nm}$=733 000 M$^{-1}$ cm$^{-1}$ for E. coli tRNA$^{Phe}$; $\varepsilon_{550nm}$=150 000/M/cm$^{-1}$ for Cy3 NHS ester and $\varepsilon_{650nm}$=250 000/M/cm for Cy5 maleimide.

Thin-Layer Chromatography

The analysis was done on silica gel F in a MeOH:CHCl$_3$:H$_2$O (2:1:1) mix. Products were analyzed under visible and UV light and by Phosphorimager Typhoon 9410.

Purification of Mutants

All mutants were purified to at least 95% purity using a slightly modified protocol of Perla-Kajan et al. (Protein Eng. Des. Sel. (2010) 23:129-136) on Ni-NTA column. In some cases, to obtain more than 98% purity, an additional purification step on Toyopearl DEAE-650 was applied. Partially purified EF-Tu (10 mg/ml stock) after the first step of Ni-NTA chromatography was diluted 1/10 in the running buffer (RB) (20 mM HEPES pH 7.7, 10 mM MgCl$_2$, 10 µM GDP) and applied on the DEAE 650 M column (1×25 cm). A gradient of 0.05-0.8 M NaCl in RB was used for the separation at a speed of 20 ml/h. EF-Tu eluted at the 0.4-0.5 M salt concentration.

Fluorescence Labeling of Elongation Factor Tu

Up to 50 nM of EF-Tu in 500 µl volume in labeling buffer, containing 50 mM HEPES pH 7.0, 30 mM KCl, 70 mM NH$_4$Cl and 7 mM MgCl$_2$ (buffer was carefully degassed before reaction) were incubated with 10 molar excess of TCEP (tris(2-carboxyethyl)phosphine) for 10 minutes at room temperature. The dye (Cy5 or QSY9 maleimide) was added from dimethylformamide stock in 10-15 molar excess, and incubated in dark under nitrogen at 25° C. for 2 hours or overnight at 4° C. Unreacted dye was separated from labeled EF-Tu on a Sephadex G-15 column (manually packed Bio-Rad column 0.5×15 cm). Fractions containing protein were concentrated on a Millipore 10 K centrifuge filter or by dialysis on Spectrapor 8 K membrane against same buffer containing 50% glycerol or 40% PEG 40000 and stored at −20° C. in 50% glycerol.

Reversed Phase Liquid Chromatography Mass Spectrometry Analysis (RPLC-MS)

The Cy5-EF-Tu E348C sample, or unlabeled protein as a control, was diluted in 100 mM NH$_4$HCO$_3$. Protein digestion was initiated by adding trypsin and incubated at 37° C. Resulting peptides were desalted using C$_{18}$ Ziptip and further separated by reversed phase liquid chromatography (RPLC) on an Ultimate 3000 LC system (Dionex, Sunnyvale, Calif., USA) coupled with an LTQ Orbitrap Velos mass spectrometer (Thermo Scientific). The eluted peptides were directly introduced into the Orbitrap via a Proxeon nano electrospray ionization source with a spray voltage of 2 kV and a capillary temperature of 275° C. The LTQ Orbitrap Velos was operated in the data-dependent mode with survey scans acquired at a resolution of 60 000 at m/z 400 (transient time=256 ms). Top 10 most abundant isotope patterns with charge ≥2 from the survey scan were selected and further fragmented in CID mode.

Data Analysis

The tandem mass spectrometry (MS/MS) spectra from liquid chromatography-tandem mass spectrometry (LCMS-MS) analyses were searched against EF-Tu sequence using Mascot (Ver. 2.3) through the Proteome Discoverer (V. 1.3, Thermo Scientific). Following search parameters were used: Cy5 (778.2837 Da) labeling of cysteine and oxidation of methionine as variable modifications; trypsin as the digestive enzyme with a maximum of two missed cleavages allowed; monoisotopic peptide precursor ion tolerance of 10 ppm; and MS/MS mass tolerance of 0.5 Da.

Relative Quantitation

Raw LCMS-MS files from LTQ Orbitrap Velos mass spectrometer were processed in Quant browser module of Xcalibur software. Extracted ion chromatograms were generated from the MS full-scans. Following parameters were used: m/z for C81_Cy (830.6873), m/z for C348_Cy (1100.1668), mass tolerance 5 ppm, smoothing enabled (type Gaussian). Relative quantitation was performed using peak areas extraction from the extracted ion chromatogram of the selected precursor ions.

Non-Enzymatic Hydrolysis Protection Assay

The assay of Cy3-labeled Phe-tRNA$^{Phe}$ in ternary complex with EF-TU and GTP was performed and evaluated as described (Pingoud et al. (1979) Anal. Biochem., 92:123-127).

Translation In Vitro

The assay of Phe-tRNA$^{Phe}$(Cy3) activity in poly(Phe) synthesis was performed as described (Perla-Kajan et al. (2010) Protein Eng. Des. Sel., 23:129-136).

Fluorescence Gel Retardation Assay

Incubation buffer included 70 mM HEPES-KOH (pH 7.6), 52 mM NH$_4$OAc, 8 mM Mg Cl$_2$, 30 mM KCl, 1.4 mM DTT, 0.1 mM GTP, 2.6% glycerol, 7.2 mM phosphoenolpyruvate and 2.5 U/ml pyruvate kinase. HPLC purified [$^{14}$C]Phe-tRNA$^{Phe}$(Cy3) [40 µM] (44 cpm/µl), dye ratio 1, was used for [1 µM] tRNA master mix. Concentration of EF-Tu preparations was varied from 1 to 12 µM in a 10 µl volume. Upon addition of EF-Tu, the reaction mix was incubated 15 minutes at 37° C. and loaded using 10× loading buffer (50% glycerol with 0.02% bromophenol blue) on 10% polyacrylamide gel electrophoresis in a running buffer (10 mM MES pH 6.0, 65 mM NH$_4$OAc, 10 mM Mg(OAc)$_2$ and 10 mM GTP). The gel was run at 4° C., ≤125V (≤40 mA for a mini gel). After the run, the gel was immediately scanned for Cy3 and Cy5 fluorescence by Typhoon 9410 using green (532 nm) or red (633 nm) lasers setup correspondingly. To monitor by autoradiography, dried gels were placed in a phosphorimager cassette or over X-ray film and left overnight.

FRET Assay (Assembly Fluorescence)

FRET measurements were done using Photon Technology International fluorescence spectrofluorometer with FeliX software. Cy3 fluorescence was monitored in the spectrum or time base mode at excitation/emission 549/565 nm. FRET upon formation of ternary complex was monitored in the time-base mode using the 532-nm excitation (Cy3 dye) and 665-nm emission (suitable for the Cy5 dye). The slot parameters and photomultiplier voltage were adjusted to get a response in the range of 0.5-1.2×10$^6$ RFU for the Cy3 fluorescence scan at the 20-30 nM Phe-tRNA$^{Phe}$(Cy3) concentration and 4-5×10$^4$ RFU for Cy5 fluorescence scan (excitation/emission 633/665 nm) at the 300-400 nM Cy5-EF-Tu concentration. The titration of Phe-tRNA$^{Phe}$(Cy3) by Cy5-EF-Tu was typically done in presence of 100 µM GTP in a 150 µl volume of the same incubation buffer as used in the above mentioned gel retardation assay. During the assay (up to 120 minutes), the reaction mix also was supplemented with 1 mM ATP and 5 µg/ml of Phe-tRNA synthetase to prevent deacylation of Phe-tRNA$^{Phe}$(Cy3). The concentration of Phe-RNA$^{Phe}$(Cy3) was up to 30 nM and GTP:Cy5-EF-Tu was varied in range of 30-240 nM.

Results

Strategy and Construction of EF-Tu Mutants

The mutants in the SAV background showed higher deacylation rate constants in non-enzymatic hydrolysis protection assays, meaning that protection against deacylation of Phe-tRNA$^{Phe}$ was reduced (Perla-Kajan et al. (2010) Protein Eng. Des. Sel., 23:129-136). The reason for this may be due to the replacement of the cysteines present in wild-type EF-Tu (C81, C137 and C255) with the Ser, Ala or Val residues, respectively, in this SAV construct. Therefore, a series of mutants was prepared in which one or more cysteines were reverted to the wild-type sequence.

One strategy for labeling of individual thiols in the EF-Tu molecule was based on eliminating of all three cysteines present in the native protein and introducing an additional cysteine residue based on the available crystal structures of EF-Tu:tRNA complexes and published functional and structural studies of EF-Tu. Also, a very short distance was demanded between the donor and acceptor fluorophores located on EF-Tu and tRNA molecules. Correspondingly, EF-Tu mutants were generated that contained single cysteine residues at 324, 325 or 348 positions in the SAV background (Perla-Kajan et al. (2010) Protein Eng. Des. Sel., 23:129-136). Despite good yield and labeling efficiency, the mutants in the SAV background showed lower binding capability to tRNA$^{Phe}$ and activity in in vitro translation assays, as well as lower ability to protect Phe-tRNA$^{Phe}$ in non-enzymatic hydrolysis protection assay (FIG. 1).

The principle of the assay is based on the fact that correctly formed complex between EF-Tu:GTP and aa-tRNA protects aa-tRNA from non-enzymatic deacylation. A radiolabeled [$^{14}$C]Phe tRNA$^{Phe}$(Cy3) or [$^{14}$C]Phe-tRNA$^{Phe}$ and the wild-type E. coli elongation factor Tu were used. [$^{14}$C]Phe-tRNA$^{Phe}$(Cy3) showed a similar behavior in non-enzymatic hydrolysis protection assay when compared with [$^{14}$C]Phe-tRNA$^{Phe}$.

To improve on the in vitro translation activity and ternary complex assembly, the K324C, G325C and E348C mutations were moved into the AV background (where the native cysteine residue was retained at position 81). When choosing this strategy, it was hypothesized that as C81 is a buried residue in EF-Tu (because of the known ternary complex structure of E. coli EF-Tu:GDPNP:kirromycin:Phe-tRNA$^{Phe}$ complex based on a PDB file 1ob2.pdb), the residue's reactivity for the incoming maleimide group should be much lower than the reactivity of the solvent-exposed second cysteine residue in the mutant EF-Tu at position 348 or 324. Thus, preferential labeling of the secondary cysteine residue should be feasible.

Figure 2:
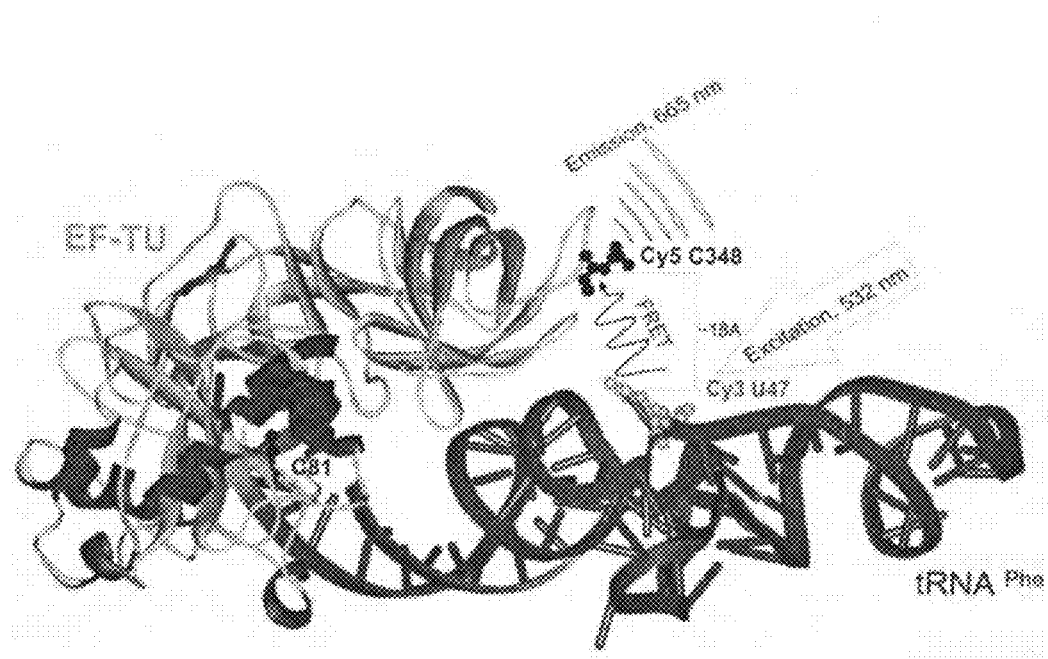

It was ascertained that the calculated distance in formed ternary complex between Cy3 labeled 3-(3-amino-3-carboxypropyl)uridine (acp$^3$U) at position 47 of tRNA$^{Phe}$ and Cy5-labeled cysteine at position 348 (or 324) of EF-Tu is sufficiently shorter than the Foster radius (56 Å) reported by the manufacturer (Amersham Biosciences) for the Cy5:Cy3 interaction (FIG. 2). The K324C and E348C EF-TuAV mutant proteins were not only active in in vitro translation, but also protected by Phe-tRNA$^{Phe}$ against non-enzymatic hydrolysis compared with wild type (FIG. 1). The same two mutants, but in the wild-type background, behave very close to wild-type EF-Tu. Therefore, the K324C (AV) and E348C (AV) mutants were chosen for further studies, involving labeling with fluorophores followed by subsequent characterization of these mutant proteins in FRET assays.

Fluorescence Labeling of tRNA

Isolation of Cy3-labeled tRNA$^{Phe}$. Current methods for chemical modification of tRNA molecules with fluorescent dyes are based on presence in certain tRNAs at their elbow positions of high reactive unusual nucleotides, such as 4-thiouridine (s$^4$U) at position 8 or 3-(3-amino-3-carboxypropyl)uridine (acp$^3$U) at position 47. Such nucleotides can be modified with maleimide or NHS-linked fluorophores (Plumbridge et al. (1980) Nucleic Acids Res., 8:827-843; Janiak et al. (1990) Biochemistry, 29:4268-4277; Blechschmidt et al. (1994) Eur. J. Biochem., 219:65-71; Blanchard et al. (2004) Proc. Natl. Acad. Sci., 101:12893-12898). After the labeling reaction is completed, excess dye can be removed by phenol extraction and ethanol precipitation, or by using gel filtration, or by a dialysis step (Walker et al. (2008) Methods, 44:81-86), followed by separation of labeled from unlabeled tRNA using RP HPLC. This chromatography is effective because the hydrophobicity of tRNA molecules after conjugation with a dye is often changed. Charging of the labeled tRNA molecule with cognate amino acid by cognate aa-tRNA synthetase is the next important step, followed by subsequent purification of charged and fluorescently labeled product. Achieving a high (close to 100%) labeling and aminoacylation rate is difficult, thus column chromatography is often essential to concentrate the desired forms. In most cases, the final purification step for labeled and aminoacylated tRNA also includes RP HPLC. The difference in retention time between charged and uncharged product is critical to isolate high-purity labeled and aminoacylated tRNA.

Standard methods for purifying fluorescently labeled tRNA$^{Phe}$ (Kothe et al. (2006) 356:148-150; Pan et al. (2009) RNA, 15:346-354) are based on using phenyl-conjugated or C18 (octadecyl group) stationary phase columns. The reported conditions did not allow for baseline separation of key components, which is needed to obtain highly purified reagents. While good separation between dye-conjugated and non-modified tRNA was obtained, the difference in retention time after/before aminoacylation needed to be increased. The HPLC procedure presented here employs a different type of reverse phase column (Waters C4 Delta Pack). Short butyl groups on C4 RP HPLC column do not have so strong reversed phase retention compared with phenyl or octadecyl groups, allowing better separation of more hydrophobic dye-conjugated tRNAs. C4 stationary phase combined with high ionic strength in mobile phase shows increased difference in the retention time between Phe-tRNA$^{Phe}$(Cy3) and tRNA$^{Phe}$(Cy3) up to base line resolution. In addition, different chromatographic conditions were developed, as described in the Methods section. The new method allows for purification of modified tRNAs in one chromatographic step in semi-preparative (mg) amounts using analytical size column.

Figure 3A:
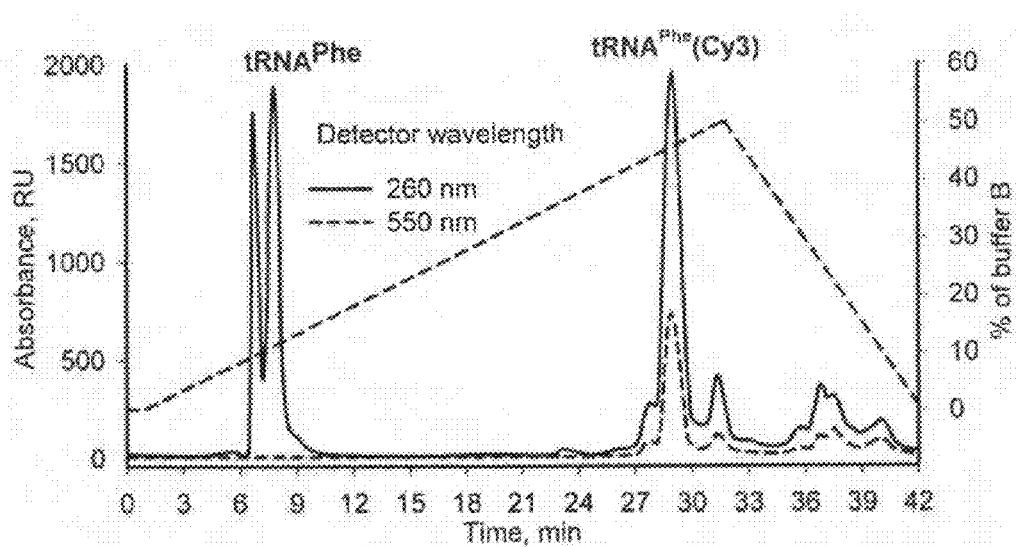
Figure 3B:
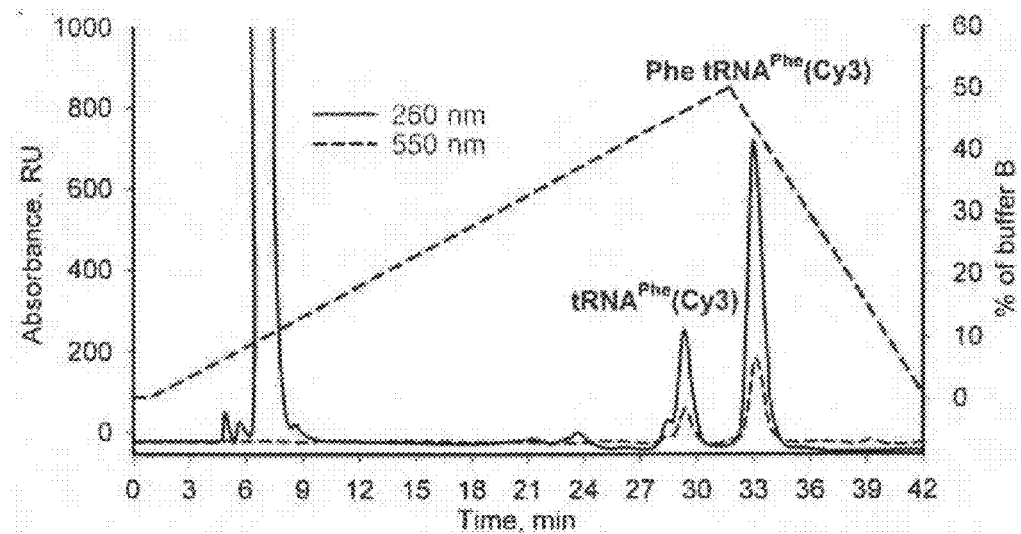

After the labeling reaction, Cy3-labeled tRNA$^{Phe}$ was purified from unmodified RNA and from free dye by RP HPLC. The unmodified E. coli tRNA$^{Phe}$ eluted in the void column volume (4 ml). The conjugation with Cy3 dye increased tRNA retention time on the column by about 20 min. Traces of free dye were efficiently removed in this step, as the Cy3 NHS ester eluted at the end of gradient and retention time was about 39 minutes (FIGS. 3A and 3B). The purified Phe-tRNA$^{Phe}$(Cy3) had a dye/tRNA ratio of 1-1.2 by UV/Vis spectrophotometry and was stored in 100 μM aliquots before the aminoacylation reaction was performed.
Purification of Aminoacylated Cy3-Labeled tRNA$^{Phe}$. Charging of the Cy3-labeled tRNA$^{Phe}$ was performed at the same conditions as described for E. coli tRNA$^{Phe}$ (Perla-Kajan et al. (2010) Protein Eng. Des. Sel., 23:129-136). Aliquots of purified tRNA$^{Phe}$(Cy3) were incubated with the recombinant Phe-tRNA synthetase in presence of [$^{14}$C]Phe or 'cold' Phe, ATP and regeneration system. The charging efficiency of the bulk fraction of tRNA$^{Phe}$(Cy3) was lower when compared with a wild-type tRNA$^{Phe}$, where percent of incorporation of [$^{14}$C]Phe was close to 90%. After the phenol extraction and ethanol precipitation, the tRNA was purified in the second round of RP HPLC under the above mentioned conditions. A 5±0.25 minute difference in retention times for the charged Phe-tRNA$^{Phe}$(Cy3) and uncharged tRNA$^{Phe}$(Cy3) was observed (FIGS. 3A and 3B). The fractions were analyzed by UV/Vis spectroscopy, scintillation counting, thin-layer chromatography (TLC) and gel electrophoresis. The analyses showed that the slower migrating peak, corresponding to Phe-tRNA$^{Phe}$(Cy3), was purified. A covalently bound tRNA$^{Phe}$(Cy3) dye was detected in two tRNA$^{Phe}$ fractions (at 28 and 33 minutes) by absorption on 550 nm as well as by TLC and gel electrophoresis, but the [$^{14}$C] Phe activity was detected only in the late (33 minutes) fraction which was also confirmed by autoradiography of a gel and TLC plate. The precipitation of tRNA was not performed before the second round of RP HPLC, because the phenol derivatives and an excess of Phe eluted at the void column volume (Table 1) which allowed reducing the purification time while increasing the yield. Importantly, the efficiency of aminoacylation of tRNA$^{Phe}$(Cy3) could be calculated from integrated peak areas and varied from 60 to 75%. Thus, because charging efficiency could be monitored directly by RP HPLC without using $^{14}$C Phe, the current RP HPLC conditions were effectively used for preparation of the 'cold' charged Phe-tRNA$^{Phe}$(Cy3).

TABLE 1

Retention time of separated compounds after labeling and charging of tRNA$^{Phe}$ on RP C4 column.

| # | Compound | Retention time (min) |
|---|---|---|
| 1 | tRNA$^{Phe}$ | 8 ± 0.5 |
| 2 | Cy3 NHS ester | 39 ± 1 |
| 3 | tRNA$^{Phe}$(Cy3) | 28 ± 0.5 |
| 4 | Phe-tRNA$^{Phe}$(Cy3) | 33 ± 0.5 |
| 5 | Phe-tRNA$^{Phe}$ | 24 ± 1 |
| 6 | Phenylalanine | 9 ± 0.5 |

In Vitro Translation Assay of Phe-tRNA$^{Phe}$ (Cy3) in Poly-Phe Synthesis.

Figures 4A, 4B:
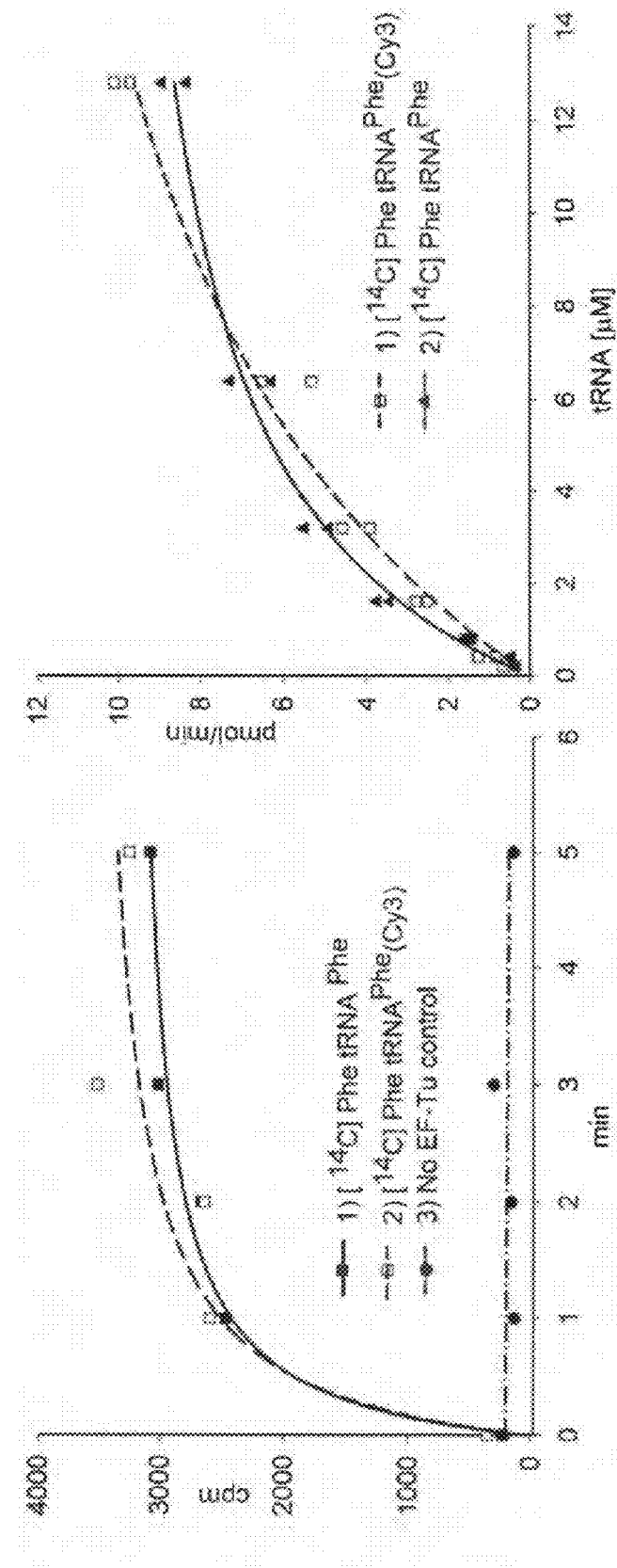

Phe-tRNA$^{Phe}$(Cy3) and Phe-tRNA$^{Phe}$ are functionally active at a similar level as shown in the experiment in which $^{14}$C Phe was incorporated into poly-Phe. The results are shown both as a function of time (FIG. 4A) or the tRNA concentration (FIG. 4B).

Labeling of EF-Tu with Cy5

Labeling efficiency of EF-Tu with maleimide conjugated fluorophores usually depends on many factors, including quality of protein prep (EF-Tu tends to form aggregates), temperature and presence of free oxygen and reducing agents in labeling buffer. The dye/protein ratio usually increases with highest temperature, but due to instability of protein, it is preferred to perform reaction overnight at 4° C. or at room temperature for 2 hours. The dye/protein ratio in this case is usually less than one; however, the protein is active in FRET assays.

Mass spectrometry evidence of labeling of E348C mutant with Cy5 maleimide. The subject of this study, EF-Tu mutant E348C, has two cysteine residues at positions 81 and 348, of which C81 is buried in the structure. Nevertheless, C81 can be chemically modified by N-ethylmaleimide (Arai et al. (1974) J. Biochem., 76:523-534; Van Noort et al. (1986) Proc. Natl. Acad. Sci., 83:4617-4621). The desired outcome of the Cy5 labeling procedure is to conjugate Cy5 to the thiol of C348, and not to modify C81 (the modification of C81 would likely destabilize the EF-Tu structure, and add complexity to the analysis of FRET data). Thus, attention was paid to implementing proper conjugation procedures that would favor labeling of C348, and to the molecular characterization of EF-Tu obtained from the conjugation.

Monoisotopic mass of Cy5 maleimide provided by GE Healthcare is 777.9 Da, which was precisely calculated as 778.2837 Da. Peptides carrying C81 (MH+1710.7572 Da, HYAHVDCPGHADYVK), Cy5-C81 (MH+2489.0409 Da), C348 (MH+2519.1957 Da, TTDVTGTIELPEGVCM-VMPGDNIK) and Cy5-C348 (MH+3297.4794 Da) were identified in two independent measurements with different batches of Cy5-labeled E348C EF-Tu. Based on the integration of the extracted ion chromatogram peaks, it was concluded that the Cy5 dye distribution in EF-Tu is 65-70% at C348, and the balance at C81 (FIG. 5). At a higher temperature during the modification reaction, the labeling distribution was more balanced. Additional matrix assisted laser desorption ionization mass spectrometry (MALDI MS) control experiments were performed using Cy5-labeled and unlabeled synthetic peptide HYAHVDCPGHADYVK, corresponding to aa 75-89 of E. coli EF-Tu, and the Cy5 dye itself, to calibrate the system.

Figure 6A:
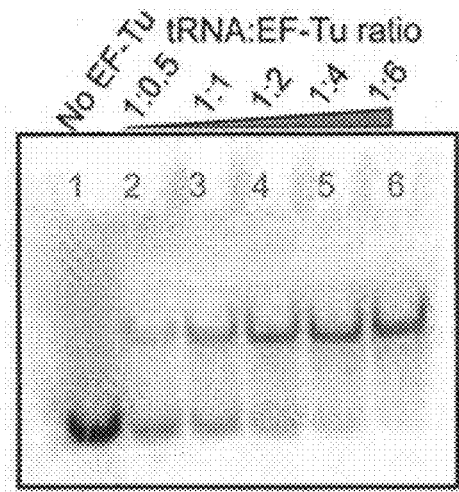
Figure 6B:
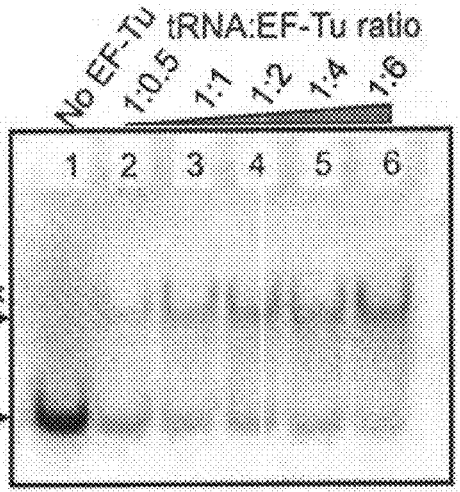
Figure 6C:
Figure 6D:
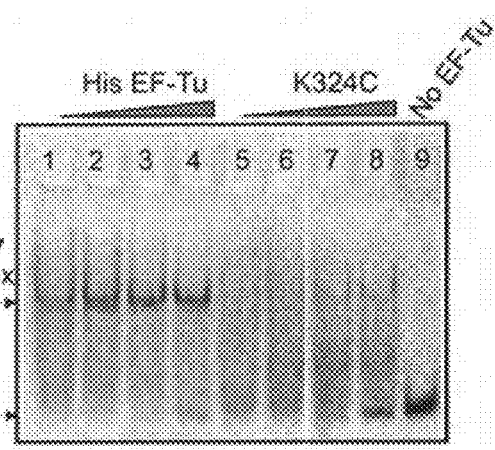

Studies of interactions of fluorescently labeled forms of EF-Tu and tRNA$^{Phe}$ Monitoring of the ternary complex formation in a gel retardation assay. The gel retardation assay was modified from methods described (Abrahams et al. (1988) Nucleic Acids Res., 16:10099-10108; Doi et al. (2007) J. Am. Chem. Soc., 129:14458-14462). Modifications included monitoring ternary complex formation by autoradiography (FIG. 6) as well as by the Cy3 and Cy5 fluorescence scan on a Typhoon 9410 scanner (FIG. 7) which effectively reduced the quantity of reagents needed, shortened the duration of the assay and eliminated experimental artifacts when compared with classical staining procedures. Autoradiography showed that recombinant EF-Tu was able to form ternary complex with labeled or unlabeled tRNA$^{Phe}$ similarly to the native protein purified from E. coli (FIGS. 6A and 6B). The K324C mutant was not as efficient in forming a solid visible band of ternary complex on the gel (FIGS. 6C and 6D), so the E348C mutant was used for further FRET studies.

Figure 7A:
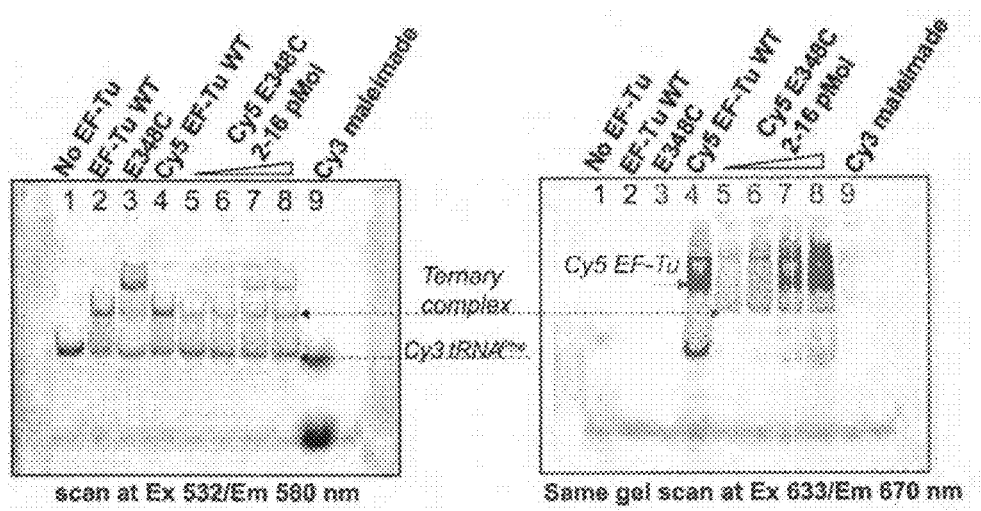
Figure 7B:
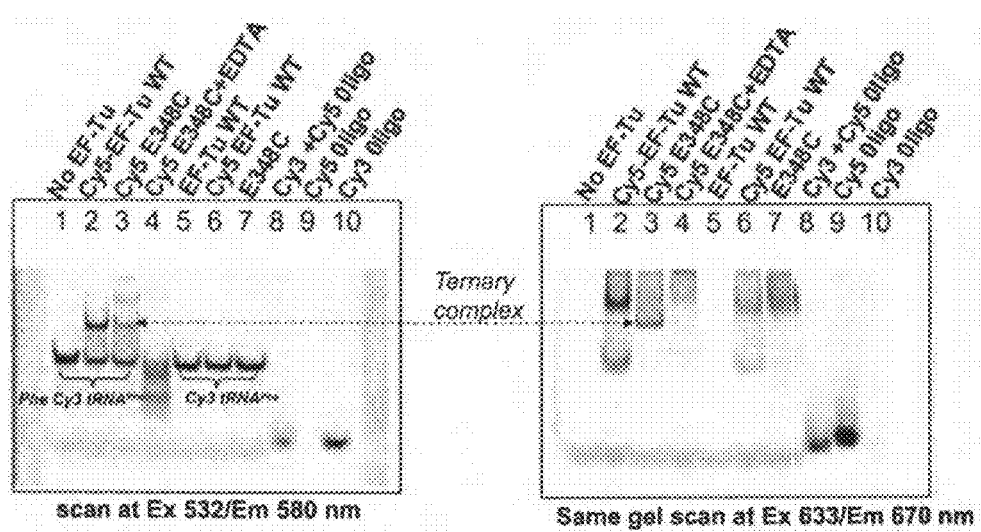

Monitoring of ternary complex formation by fluorescence scanning of the native gel has a lot of advantages, including the possibility of directly seeing labeled molecules or their complexes and a shorter time required for the experiment (FIG. 7). The total Cy3 fluorescence intensity of the labeled tRNA in the ternary complex with Cy5-EF-Tu E348C was decreased by 24-27% (the calculation was based on the integration of the bands in lines 1, 2 vs. lines 5, 6 (panel a) and line 1 vs. line 3 (panel b)). The quenching of Cy3 fluorescence in the complex was close to 60%; the calculation was based on the intensity of the ternary complex itself (compare the ternary complex bands in lines 2, 4 and 5, 6 in panel a, as well as lines 2 and 3 in panel b). Approximately 46% of labeled tRNA$^{Phe}$ was deacylated after the reaction, and migrated as free tRNA in line 1. Quite importantly, no complex formation was observed when uncharged Cy3-labeled tRNA$^{Phe}$ (lines 5, 6 and 7) was used, providing evidence for the assay specificity.

Figures 8A, 8B:
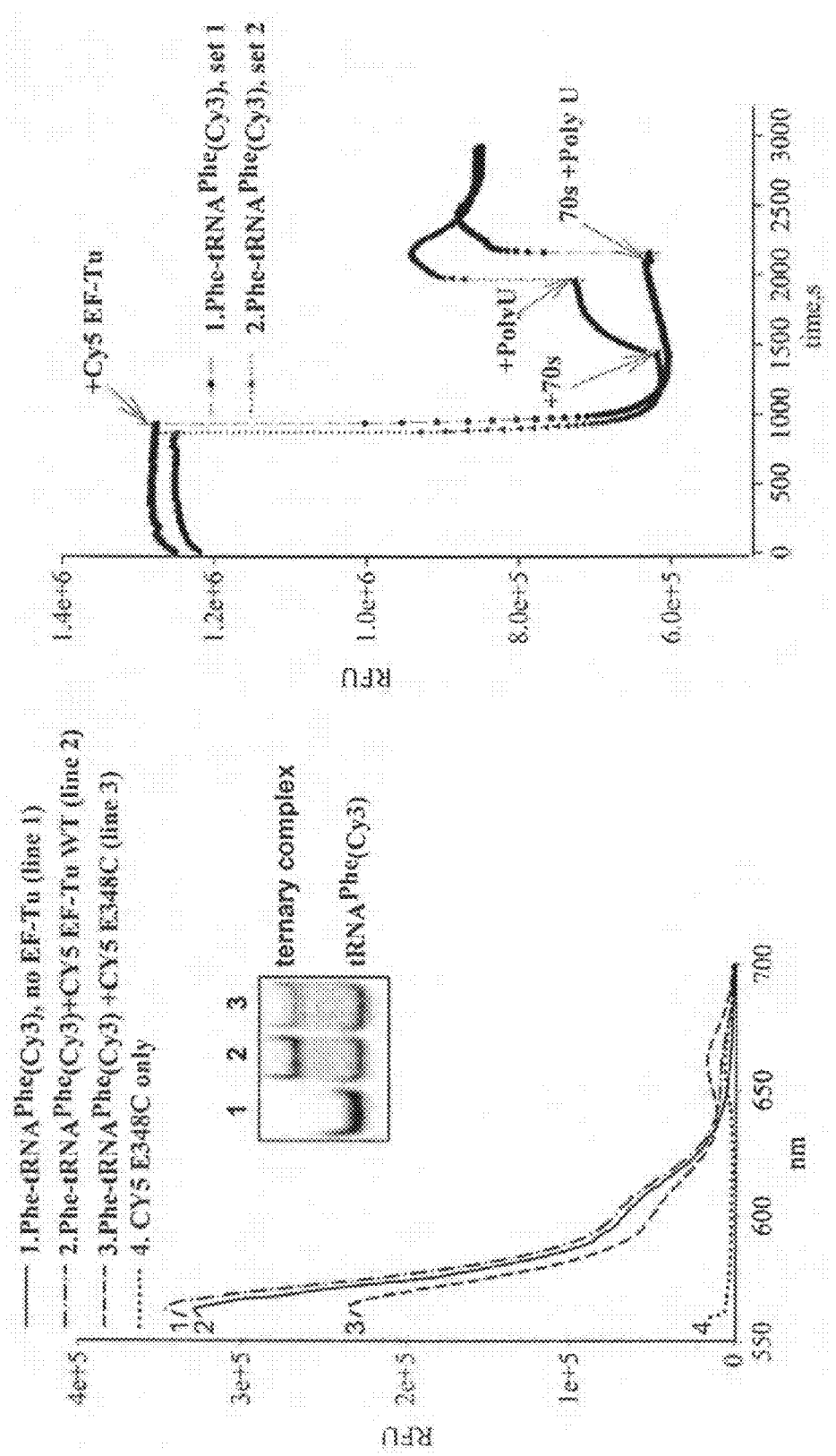

Evidence for FRET between fluorescently labeled EF-Tu and tRNA. Decrease of Cy3 fluorescence upon forming of ternary complex with GTP Cy5-labeled EF-Tu and aminoacylated tRNA was demonstrated in a series of titration experiments (FIG. 8). Based on the spectrofluorimeter data, the total decrease ternary of Cy3 fluorescence of the Phe-tRNA$^{Phe}$(Cy3) (563 nm) upon formation of the complex with Cy5 EF-Tu E348C mutant was about 29%. At the same time, Cy5 fluorescence (665 nm) increased 2.8-fold (FIG. 8A). Interestingly, the decrease of Cy3 intensity was also observed directly on a native gel, when we simultaneously monitored the ternary complex formation by gel retardation assay (FIG. 8, inset, intensity of ternary complex line 2 vs. line 3). Native EF-Tu that underwent the Cy5 labeling reaction had no quenching effect on the Cy3 fluorescence. In a control experiment, no FRET was seen in the presence of EDTA, RNAse A or proteinase X.

Figure 9:
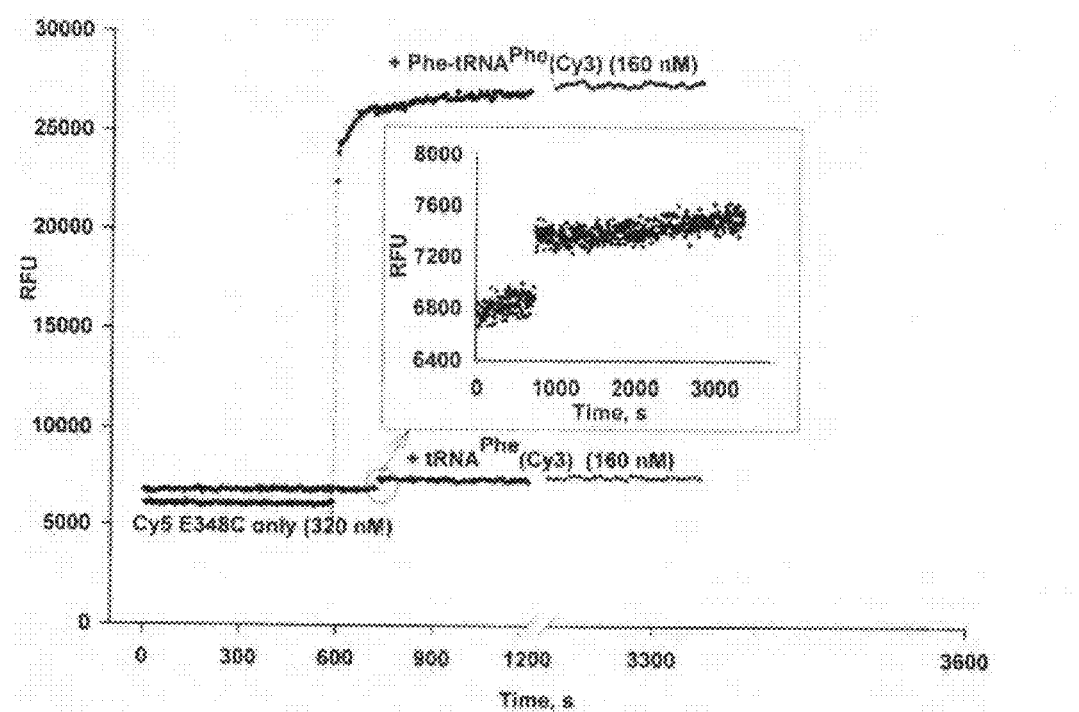
Figure 10:
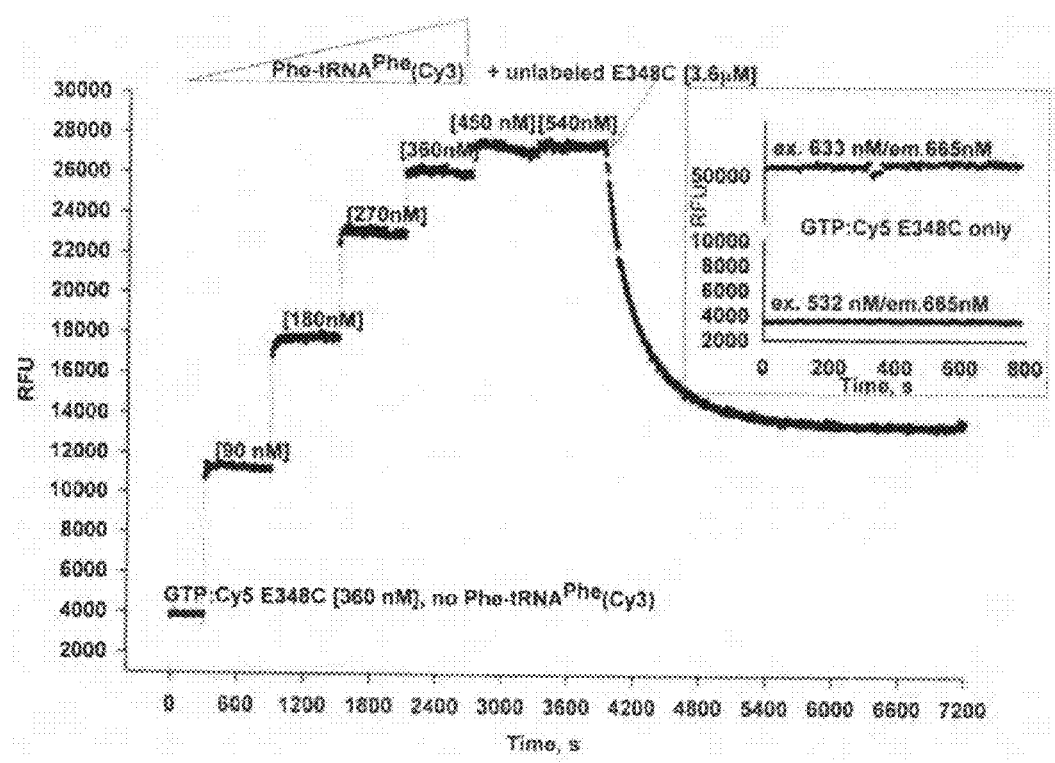

Additional evidence of FRET between charged and Cy3-labeled tRNA$^{Phe}$ and GTP form of E348C (AV) mutant was shown in a series of experiments in which the Cy5-EF-Tu emission was monitored at 665 nm while the excitation of Cy3 was at 532 nm. An approximately 5-fold increase in the Cy5 fluorescence was observed upon an addition of Phe-tRNA$^{Phe}$(Cy3) to the Cy5-labeled E348C mutant (FIG. 9). In a control experiment, the same amount of uncharged tRNA$^{Phe}$(Cy3) had almost no effect on the Cy5 fluorescence (inset). The GTP-bound form of Cy5-E348C was titrated by increasing concentrations of Phe-tRNA$^{Phe}$(Cy3) while the EF-Tu:tRNA ratio was in the 4:1 to 1:1.5 range (FIG. 10).

Figures 11A, 11B:
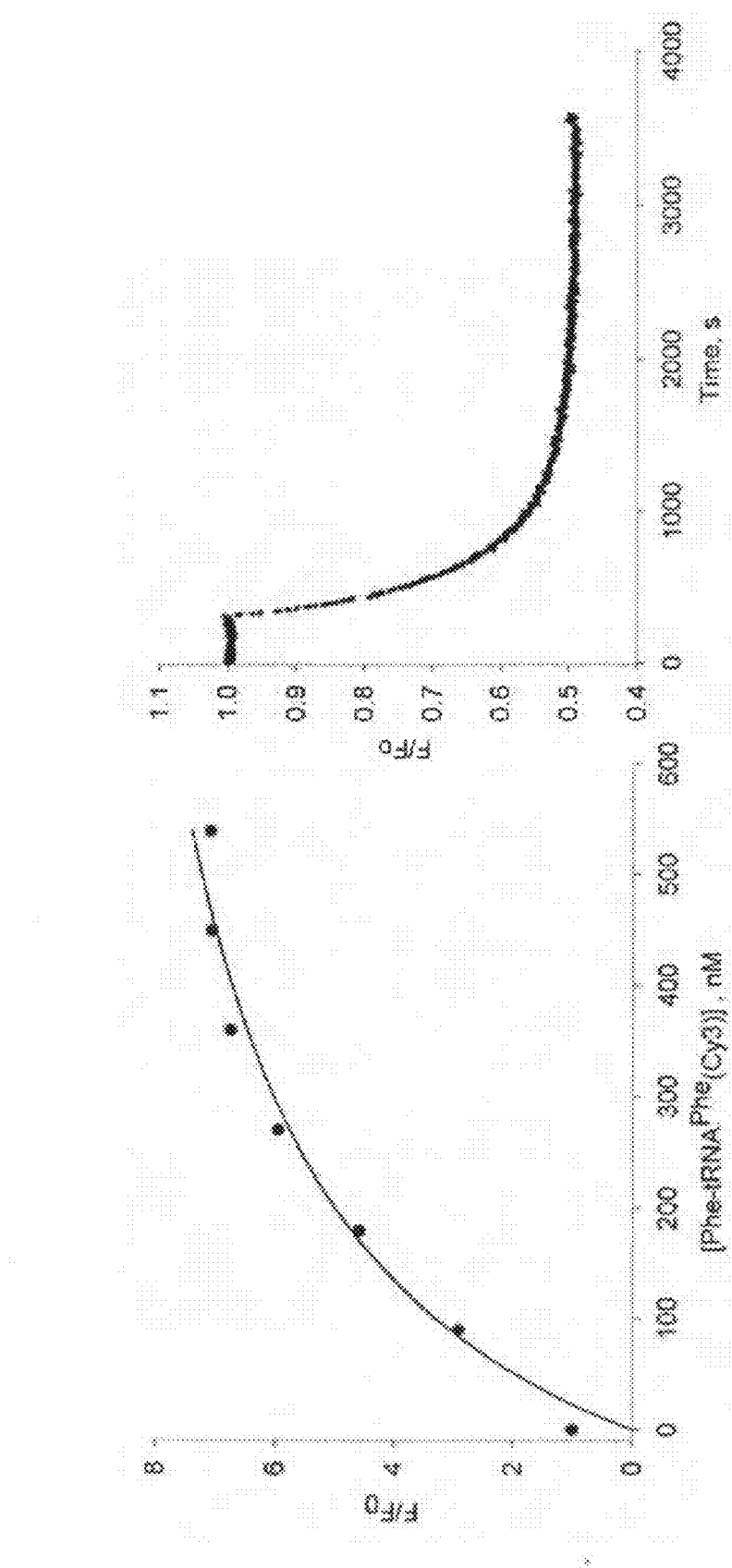

Importantly, the maximum FRET ratio, approximately 7-fold increase in Cy5 fluorescence, was observed at almost equimolar concentrations, confirming the correct complex stoichiometry. Moreover, addition of excess of unlabeled EF-Tu E348C slowly displaces the Cy5-labeled form from the ternary complex (FIG. 10, arrow, and FIG. 11B).

A nonlinear analysis of the titration data was done, similar to that described (Abrahamson et al. (1985) Biochemistry, 24:692-700; Ott et al. (1990) Nucleic Acids Res., 18:437-441), and yielded a dissociation constant of 11 nM for the ternary complex in current experimental conditions (FIG. 11A).

Figure 12:
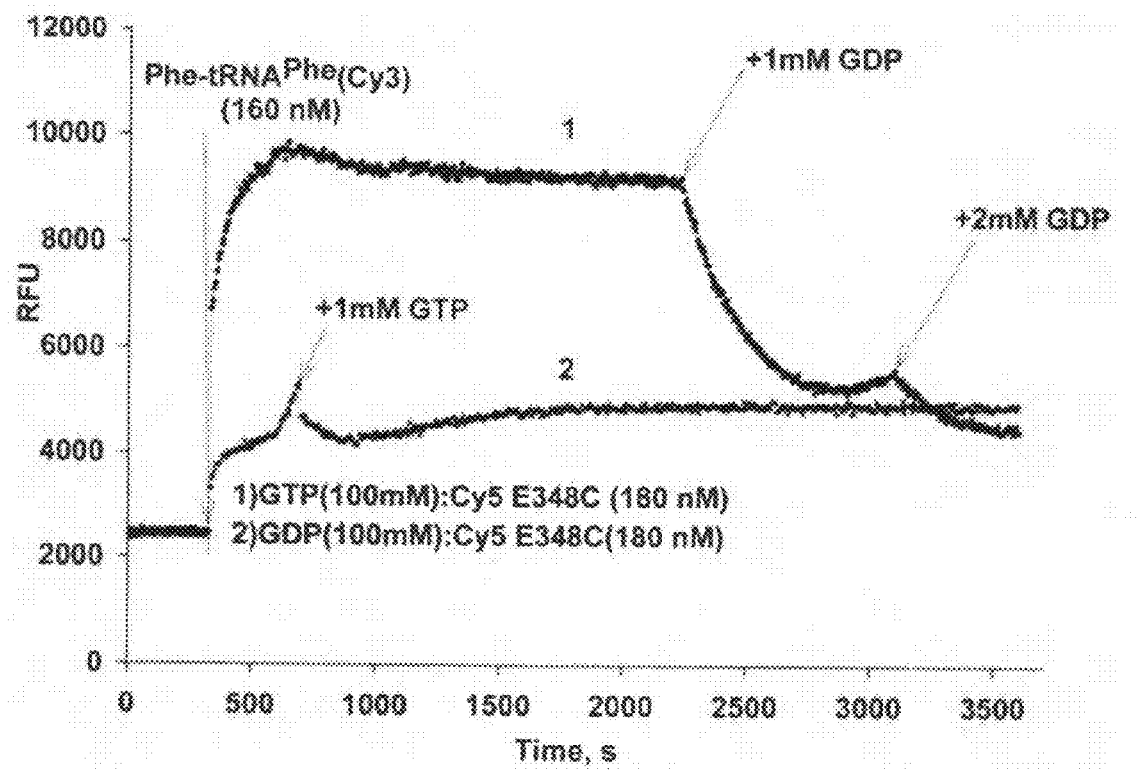

Also, addition of a 10-fold molar excess of GDP led to 60% decrease in Cy5 fluorescence in the formed complex; a similar picture was observed when Cy5 EF-Tu was preincubated with GDP (FIG. 12).

These data provide direct evidence of efficient FRET in the GTP:Cy5 E348C:Phe-tRNA$^{Phe}$(Cy3) ternary complex.

This study shows the creation of an efficient system for monitoring of ternary complex formation by FRET, using both fluorescently labeled tRNA and elongation factor Tu. Fluorescently labeled tRNA was successfully used in FRET and smFRET studies of translation machinery (Rodnina et al. (1996) J. Biol. Chem., 271:646-652; Chen et al. (2011) Mol. Cell, 42:367-377; Mittelstaet et al. (2011) J. Biol. Chem., 286:8158-8164), but use of elongation factor Tu in FRET had not been reported. Despite the fact that elongation factor Tu is a relatively small (43 kD) protein, it has a three-domain structure that has conformational flexibility (Kavaliauskas et al. (2012) Biochemistry, 51:2642-2651) and three reactive cysteine residues in positions 81, 137 and 255, which complicates labeling stoichiometry and subsequent FRET studies. The replacement of native cysteines and creating of EF-Tu mutants K324C, G325C and E348C (SAV background) did not change sufficiently their functional properties, making them an excellent candidates for FRET assay (Perla-Kajan et al. (2010) Protein Eng Des Sel, 23:129-136). Nonetheless, low FRET efficiency was initially observed upon formation of ternary complex between Cy3-labeled tRNA$^{Phe}$ and these mutants, which were labeled ether with, Dabsyl plus, QSY9, QSY7 or Cy5 dyes, despite dye/protein ratio which was close to 1/1.

To overcome these difficulties, the native cysteine residue at position 81 was retained as it was considered critical for tRNA binding (Miller et al. (1971) Arch. Biochem. Biophys., 144:115-121; Arai et al. (1974) J. Biochem., 76:523-534; De Laurentiis et al. (2011) Biochim. Biophys. Acta, 1814:684-692), and a number of functional tests using mutated and wild-type forms of protein were performed. All constructs contain a C-terminal His tag. The His tag was not removed during purification, because introducing this tag did not affect significantly correct recombinant protein folding and its ability to form ternary complex, which was proved in experiments with commercially available EF-Tu from *E. coli* as a control.

The formation in vitro of functional fluorescently labeled ternary complex also depends on many factors, including labeling efficiency of Cy5 EF-Tu and tRNA$^{Phe}$(Cy3), GTP preparation purity, charging efficiency of Phe-tRNA$^{Phe}$(Cy3) and conformation stability its components in certain reaction conditions. For this purpose, the existing method of purification of aminoacylated Phe-tRNA$^{Phe}$(Cy3) was improved, allowing for 100% labeled and charged functionally active tRNA. Commercially available GTP was also further purified, using ion exchange chromatography with LiCl gradient on DOWEX 1×2 resin to remove any traces of GDP/GMP from the prep.

Characterization of Cy3-Labeled tRNA and Cy5-Labeled EF-Tu

The labeling and charging efficiency of Phe tRNA$^{Phe}$ (Cy3) was close to 100% and was proven by spectroscopy, TLC, gel electrophoresis with subsequent fluorescence scanning and autoradiography. Interestingly, the collected uncharged Cy3 tRNA$^{Phe}$ fraction after charging reaction and HPLC separation could not be further aminoacylated using Phe-tRNA synthetase; this shows that a certain amount of tRNA$^{Phe}$ after conjugation with dye lost its native conformation, possibly due to side reaction of the NHS group, and can no longer be a substrate for the Phe-tRNA synthetase. The maximum efficiency of aminoacylation was close to 75%. The charged Phe-tRNA$^{Phe}$(Cy3) was fully active in in vitro translation, non-enzymatic hydrolysis protection assays and ternary complex formation.

Data from MALDI MS showed that both cysteine residues in Cy5-labeled EF-Tu at positions 348 and 81 were labeled in ratio 60-70% and 30-40%, respectively. The double-labeling was also proven by treatment of Cy5-modified EF-Tu ether with thrombin (generates 24.48 kD N-terminal peptide and 19.46 kD C-terminal), IBZA (iodosobenzoic acid; generates [1-184]-20.1 kD and [185-399] 23.84 kD peptides) or NTCB (2-nitro-5-thiocyanobenzoic acid; generates [1-81]-8.85 kD, [82-348]-29.46 kD and [349-399]-5.56 kD peptides). The preparations were analyzed on sodium dodecyl sulphate polyacrylamide gel electrophoresis and scanned for Cy5 fluorescence. Assuming that both cysteines in E348C (AV) mutant can be labeled, the protein prep after modification is a mixture of certain amount of unlabeled form, a form labeled in two positions (C81 and 348), and forms either labeled at C81 or C348. Only the last form should be 100% functionally active in FRET assay, judging 18 A distance between donor and acceptor (FIG. 2). Double-labeled (Cy5-81, Cy5-348) protein can be removed by passing through thioporyl-sepharose column, which binds free SH groups, resulting in better FRET efficiency.

Ternary Complex Formation: Gel Retardation Assay

The main advantage of the modified gel-shift assay is the possibility to directly observe ternary complex either by autoradiography or by fluorescence scan using $^{14}C$ Phe charged Phe-tRNA$^{Phe}$(Cy3). In the experimental conditions, complex always migrates between EF-Tu (top) and tRNA itself (bottom) (FIGS. 6 and 7). In the case of molar excess of E348C mutant over tRNA, additional slowly migrated bands are observed, probably due to oligomerization of EF-Tu (Ehrenberg et al. (1990) J. Mol. Biol., 211:739-749). Importantly, FRET can be observed directly on the gel, and ternary complex band of Cy5-labeled E348C is both visible with scanning by green (532 nm) and red excitation (633 nm) lasers. Complex band with unlabeled EF-Tu or with Cy5 labeled EF-TU WT can be visible only with Cy3 emission scan. No complex formed when using deacylated tRNA, or in the presence of EDTA.

Assembly FRET Assay

FRET between Phe-tRNA$^{Phe}$(Cy3) (donor) and Cy5 E348C (acceptor) was observed in a series of titration experiments. It was monitored how Cy3 fluorescence of Phe-tRNA$^{Phe}$(Cy3) was quenched upon addition of Cy5 E348C, or directly observed FRET, illuminating Cy5 EF-Tu with green light and observed Cy5 emission. In both cases, direct evidence of FRET was observed. Duration of measurements in time base mode was up to 2 hours, no significant photo bleaching effects on measurements were observed. Cy3 fluorescence was sharply decreased (up to 50-60%) upon addition of Cy5 E348C. On the other hand, excitation of Cy5 EF-Tu with green light shows 5-7-fold increase of Cy5 emission in presence charged Phe-tRNA$^{Phe}$ (Cy3).

Energy transfer efficiency (E) was calculated based on data presented in FIG. 8B using equation (Lakowicz and Joseph, 1999): $E=1-[(Fda-Fd\cdot(1-fa))/Fd\cdot fa$, where Fda is integrated fluorescence intensity of Phe tRNA$^{Phe}$(Cy3) in presence of Cy5 EF-Tu; Fd is an integrated fluorescence intensity in the absence of Cy5 EF-Tu and fa is fractional labeling of Cy5 EF-Tu. In current experimental conditions E=0.74.

Negative controls with deacylated tRNA, absence of GTP, presence of proteinase or RNAse, showed no FRET. Addition of excess of unlabeled EF-Tu to preformed complex led to exponential decrease in Cy5 fluorescence, due to displacement of labeled form by unlabeled one. Similar picture was observed in presence of excess of GDP, when GTP:EF-Tu converted to GDP form, with low affinity to tRNA and the complex decays. The in vivo situation is opposite, because the intracellular concentration of GTP is approximately nine times higher than GDP, so complex formation is favorable (Kavaliauskas et al. (2012) Biochemistry, 51:2642-2651). This assay also can be used to monitor in vitro translation reaction. An addition of 70S ribosome preparation led to increased Cy3 and decreased Cy5 fluorescence, because donor and acceptor become spatially separated upon EF-Tu dissociation from the ribosome. The system presented here, with E348C mutant of EF-TuAV, can be efficiently used to study protein synthesis.

EXAMPLE 2

Assay Configuration

All FRET measurements were done using PTI (Photon Technology International) fluorescence spectrofluorometer with FeliX 1.42B software. The FRET was monitored in the time-base mode using the 532 nm excitation and 665 nm emission (suitable for the Cy5 dye). The slot parameters and photomultiplier voltage were adjusted to get a response in the range of $2.6-3\times10^3$ RFU for the Cy5 fluorescence at a 200 nM concentration of Cy5-labeled EF-Tu. Time-base titration experiments were typically carried out in a 150 µl black cuvette at 25 or 37° C. The Cy5 fluorescence was monitored at five second intervals for up to 2 hours. Cy5-labeled EF-Tu carrying the E348C mutation was added from a concentrated stock solution to reach the final concentration of 180-200 nM.

Key Reagents

The 5× incubation buffer was 350 mM HEPES-KOH (pH 7.6), 260 mM NH$_4$OAc, 40 mM Mg(OAc)$_2$, 150 mM KCl, 7 mM DTT and 12.6% glycerol. The 1× incubation buffer in final reaction volume was also supplemented with 1 mM ATP and 5 µg/ml of Phe-tRNA synthetase, 7.2 mM phosphoenolpyruvate and 2.5 U/ml pyruvate kinase; a 40 µM stock of Cy3-labeled aminoacylated tRNA$^{Phe}$, a 30 µM stock of Cy3-labeled uncharged tRNA$^{Phe}$, a 110 µM stock of Cy5-labeled EF-Tu [C137A, C255V, E348C], a 5 mg/ml stock of Phe-tRNA synthetase, and a 10 mM stock in DMSO (7.97 mg/ml) of Kirromycin (FW 796.9).

Results

Figure 13:
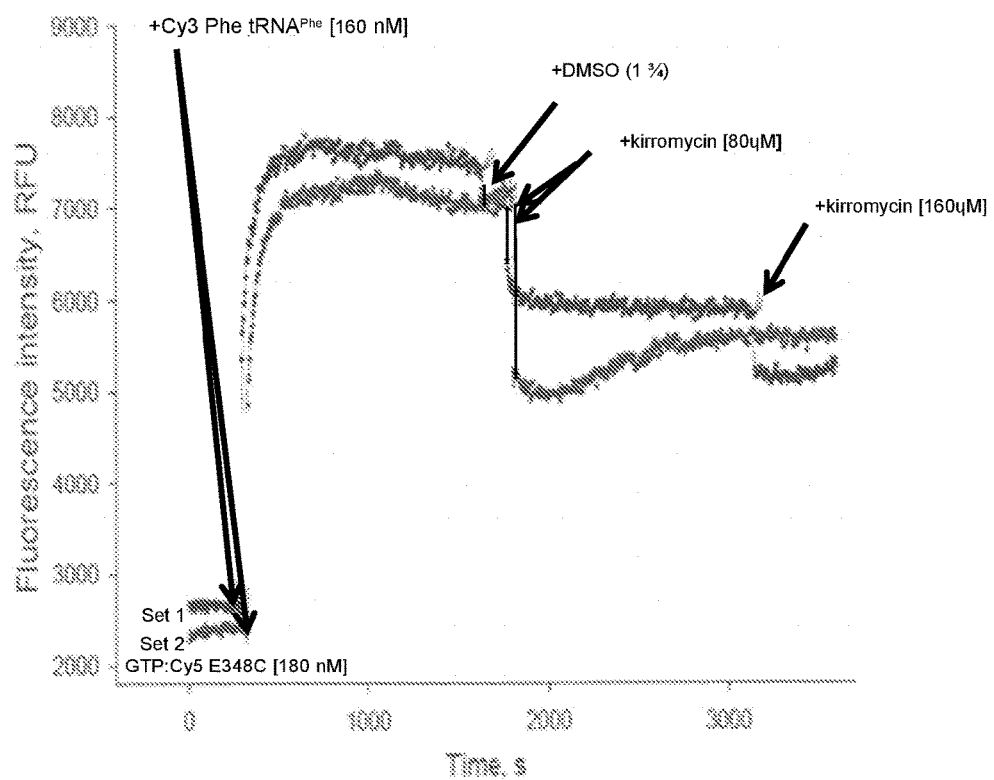
FIG. 13 shows the direct effect of kirromycin on complex formation. The addition of the inhibitor kirromycin significantly reduces the fluorescence intensity in the assay.

FIG. 13 shows a direct effect of kirromycin on complex formation. The addition of an inhibitor (kirromycin) significantly reduces the fluorescence intensity in the assay. The Cy5-labeled EF-Tu [180 nM] (GTP form) in a 300 µl volume was placed in 1× incubation buffer. The volume was split into two parts and measured in two sets at 25° C. Addition of Cy3-PhetRNA$^{Phe}$ [160 nM] after 5 minutes of incubation increased the Cy5 fluorescence approximately three times. The FRET response was decreased approximately 30% after addition of kirromycin [80 µM].

As explained above, FIG. 12 shows displacement of GTP:EF-Tu from the ternary complex. An addition of an inhibitor (GDP) significantly reduces the fluorescence intensity in the assay—see the black line (Cy5 fluorescence only, Ex 534/Em 665 nm). The Cy5-labeled EF-Tu [180 nM] (GTP form) in a 300 µl volume was placed in 1× incubation buffer. The reaction was split into two parts and supplemented with 100 µM GTP (Set I) or GDP (Set II). The fluorescence intensity was measured at 25° C. The results for set I show an approximately 4-fold increase in the Cy5 fluorescence upon an addition of Cy3-PhetRNA$^{Phe}$ [160 nM]. The addition of a 10-fold molar excess of GDP led to a 60% decrease in the Cy5 fluorescence. When the Cy5-labeled EF-Tu was incubated with GDP (set II), the FRET response was significantly lower.

Figure 14:
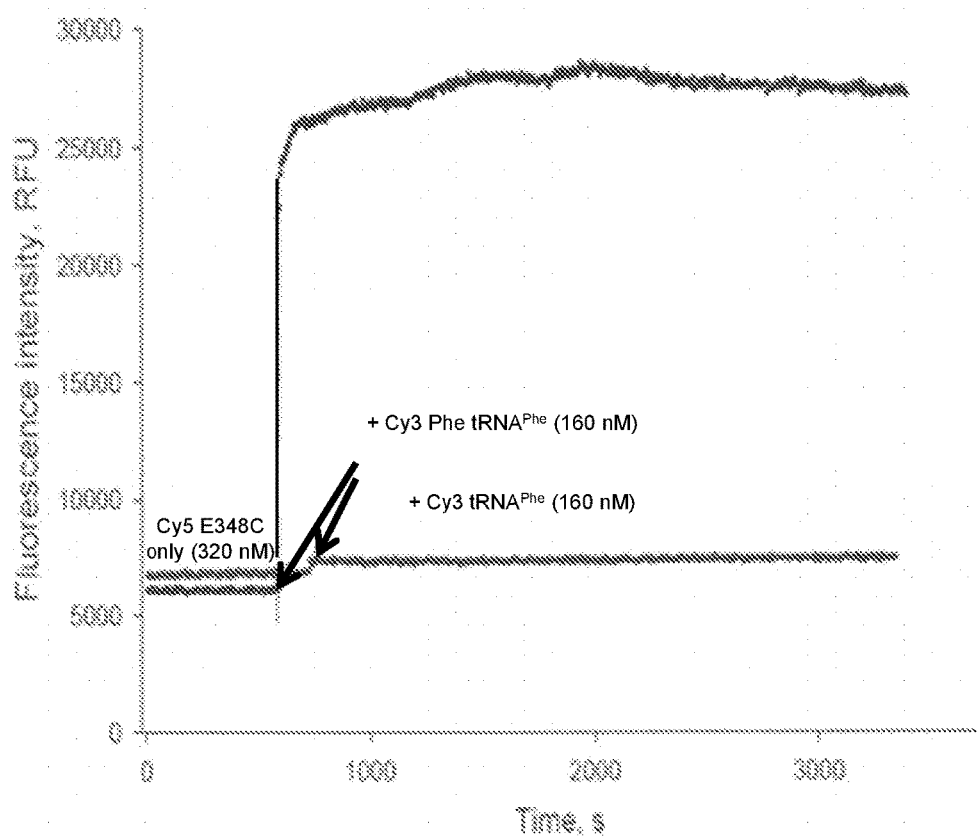
FIG. 14 shows the effect of aminoacylation of Cy3-tRNA on complex formation. In this control experiment it is shown that non-aminoacylated tRNA$^{Phe}$ is inactive in the assay and does not bind to EF-Tu.

FIG. 14 shows the effect of aminoacylation of Cy3-tRNA on complex formation. In this control experiment, it is shown that non-aminoacylated tRNA$^{Phe}$ is inactive in the assay and does not bind to EF-Tu. The Cy5-labeled EF-Tu [320 nM] (GTP form) was in a 300 µl volume of the 1× incubation buffer. The reaction was supplemented with 100 µM GTP and split on two parts. Set one (black) showed a 4.7-fold increase in the Cy5 fluorescence upon an addition of Cy3-PhetRNA$^{Phe}$ [160 nM]. In set two, an addition of the same amount of uncharged Cy3-tRNA$^{Phe}$ did not have a significant effect on the Cy5 fluorescence due to the absence of FRET.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method of identifying whether a test compound is a potential candidate having antimicrobial activity, said method comprising:
   a) mixing an elongation factor Tu (EF-Tu) mutant protein with GTP and an aminoacylated transfer RNA (aa-tRNA) in the presence and absence of a test compound and mixing said EF-Tu mutant protein with GTP and said aa-tRNA in the presence of a control compound, thereby forming a first mixture comprising said EF-Tu mutant protein, GTP, said aa-tRNA and said test compound, a second mixture without said test compound comprising said EF-Tu mutant protein, GTP, and said aa-tRNA, and a third mixture comprising said EF-Tu mutant protein, GTP, said aa-tRNA and said control compound, wherein said EF-Tu mutant protein is operably linked to a first energy transfer pair member, which comprises a fluorescent dye, wherein said aa-tRNA is operably linked to a second energy transfer pair member, which comprises a fluorescent dye, and wherein said first energy transfer pair member and said second energy transfer pair member form a fluorescence resonance energy transfer ("FRET") pair, wherein said first energy transfer pair member is a FRET donor of the FRET pair and said second energy transfer pair member is a FRET acceptor of the FRET pair or said first energy transfer pair member is a FRET acceptor of the FRET pair and said second energy transfer pair member is a FRET donor of the FRET pair;
   b) detecting the fluorescence emitted from the FRET acceptor in each of said first mixture, said second mixture, and said third mixture and comparing the fluorescent level of the FRET acceptor in said first mixture to the fluorescent level of the FRET acceptor in said second mixture and the fluorescent level of the FRET acceptor in said third mixture; and
   c) identifying the potential candidate having antimicrobial activity based on results obtained from the comparing step, wherein a drop in the fluorescent level of the FRET acceptor fluorescence in the first mixture relative to the fluorescent level of the FRET acceptor fluorescence in the second mixture indicates that said test compound interferes with the formation of a ternary complex comprising said EF-Tu mutant protein, GTP, and said aa-tRNA complex, and is a potential candidate having antimicrobial activity; and
   wherein said EF-Tu mutant protein has EF-Tu functions, comprises a protein sequence having 90% homology or more than 90% homology to SEQ ID NO:1, and comprises a cysteine at position 81, a non-cysteine residue at position 137, a non-cysteine residue at position 255, and a cysteine at position 348 linking to said first FRET energy transfer member.

2. The method of claim 1, wherein the second energy pair member is operably linked to position 47 of said aa-tRNA.

3. The method of claim 1, wherein said first energy pair member is Cy3 and said second energy pair member is Cy5.

4. The method of claim 1, wherein said first energy pair member is Cy5 and said second energy pair member is Cy3.

5. The method of claim 1, wherein said EF-Tu mutant protein has three substitutions: C137A, C255V, and E348C.

6. The method of claim 1, wherein said EF-Tu mutant protein comprises an amino acid sequence having SEQ ID NO:1.

7. The method of claim 1, wherein said EF-Tu mutant protein comprises sequence having 95% homology or more than 95% homology to SEQ ID NO:1.

8. A protein having EF-Tu functions and comprising a protein sequence having 90% homology or more than 90% homology to SEQ ID NO: 1, wherein the protein further comprises a cysteine at position 81, another cysteine at a position suitable for a FRET energy transfer member for measuring an interaction of the protein with an aa-tRNA by FRET, a non-cysteine residue at position 137, and a non-cysteine residue at position 255, wherein said another cysteine is modified with a fluorescent dye suitable for FRET and is located at position 348.

9. The protein of claim 8, wherein said protein comprises three substitutions: C137A, C255V, and E348C.

10. The protein of claim 8, wherein said protein comprises an amino acid sequence having SEQ ID NO: 1.

11. The protein of claim 8, wherein the protein comprises a sequence having 95% homology to SEQ ID NO: 1.

12. A protein having EF-Tu functions and comprising a protein sequence having 90% homology or more than 90% homology to SEQ ID NO: 1, wherein the protein further comprises a cysteine at position 81, another cysteine at a position suitable for a FRET energy transfer member for measuring an interaction of the protein with an aa-tRNA by FRET, a non-cysteine residue at position 137, and a non-cysteine residue at position 255, and said another cysteine is located at position 348.

* * * * *